US009826889B2

(12) United States Patent
Haque et al.

(10) Patent No.: US 9,826,889 B2
(45) Date of Patent: Nov. 28, 2017

(54) DISPLAY DEVICE, MEDICAL DEVICE, DISPLAY METHOD AND PROGRAM

(71) Applicants: GE MEDICAL SYSTEMS GLOBAL TECHNOLOGY COMPANY, LLC, Waukesha, WI (US); Shiga University of Medical Science, Otsu, Shiga (JP)

(72) Inventors: Hasnine Haque, Tokyo (JP); Shigeyuki Naka, Shiga (JP); Shigehiro Morikawa, Shiga (JP); Tohru Tani, Shiga (JP)

(73) Assignees: Shiga University of Medical Science, Otsu, Shiga (JP); GE Medical Systems Global Technology Company, LLC, Waukesha, WI (US)

( * ) Notice: Subject to any disclaimer, the term of this patent is extended or adjusted under 35 U.S.C. 154(b) by 191 days.

(21) Appl. No.: 14/437,728

(22) PCT Filed: Oct. 15, 2013

(86) PCT No.: PCT/JP2013/077928
§ 371 (c)(1),
(2) Date: Apr. 22, 2015

(87) PCT Pub. No.: WO2014/065154
PCT Pub. Date: May 1, 2014

(65) Prior Publication Data
US 2015/0272427 A1  Oct. 1, 2015

(30) Foreign Application Priority Data

Oct. 22, 2012 (JP) ................... 2012-233156

(51) Int. Cl.
*A61B 1/045* (2006.01)
*A61B 1/00* (2006.01)
(Continued)

(52) U.S. Cl.
CPC ............ *A61B 1/045* (2013.01); *A61B 1/0005* (2013.01); *A61B 1/00045* (2013.01);
(Continued)

(58) Field of Classification Search
CPC ..... A61B 1/0005; A61B 1/045; G01B 11/254; G06T 11/00; H04N 5/23293
See application file for complete search history.

(56) References Cited

U.S. PATENT DOCUMENTS 6,221,007 B1 *  4/2001  Green ................ A61B 1/00052
600/104
2007/0173694 A1    7/2007  Kiyoshi et al.
(Continued)

FOREIGN PATENT DOCUMENTS

CN    101026988 A    8/2007
CN    102170835 A    8/2011
(Continued)

OTHER PUBLICATIONS

International Search Report issued for International Application No. PCT/JP2013/077928 dated (Jan. 21, 2014).

*Primary Examiner* — Huy T Nguyen
(74) *Attorney, Agent, or Firm* — Armstrong & Teasdale LLP

(57) ABSTRACT

A display device configured to display an endoscopic image obtained by an endoscope for observing an object is provided. The display device includes a projecting unit configured to project coordinate axes set to the object onto the endoscopic image, and a display unit configured to display thereon the endoscopic image and the coordinate axes projected onto the endoscopic image.

14 Claims, 51 Drawing Sheets

(51) Int. Cl.
  *G06T 11/00* (2006.01)
  *G01B 11/25* (2006.01)
  *H04N 5/232* (2006.01)
  *A61B 5/055* (2006.01)

(52) U.S. Cl.
  CPC ............ *G01B 11/254* (2013.01); *G06T 11/00* (2013.01); *H04N 5/23293* (2013.01); *A61B 5/055* (2013.01); *G06T 2210/41* (2013.01)

(56) References Cited

U.S. PATENT DOCUMENTS

| | | | | |
|---|---|---|---|---|
| 2009/0299142 | A1* | 12/2009 | Uchiyama | A61B 1/00158 600/118 |
| 2010/0204545 | A1* | 8/2010 | Tanaka | A61B 1/0005 600/109 |
| 2011/0245660 | A1 | 10/2011 | Miyamoto | |
| 2011/0275896 | A1* | 11/2011 | Tanaka | A61B 1/00006 600/118 |

FOREIGN PATENT DOCUMENTS

| | | |
|---|---|---|
| CN | 102196761 A | 9/2011 |
| JP | 62209481 A | 9/1987 |
| JP | H01269986 A | 10/1989 |
| JP | H0762793 B2 | 7/1995 |
| JP | 2001104333 A | 4/2001 |
| JP | 2003123097 A | 4/2003 |
| JP | 2006116289 A | 5/2006 |
| JP | 2007007041 A | 1/2007 |
| JP | 2009172050 A | 8/2009 |
| WO | 2006070669 A1 | 7/2006 |

\* cited by examiner

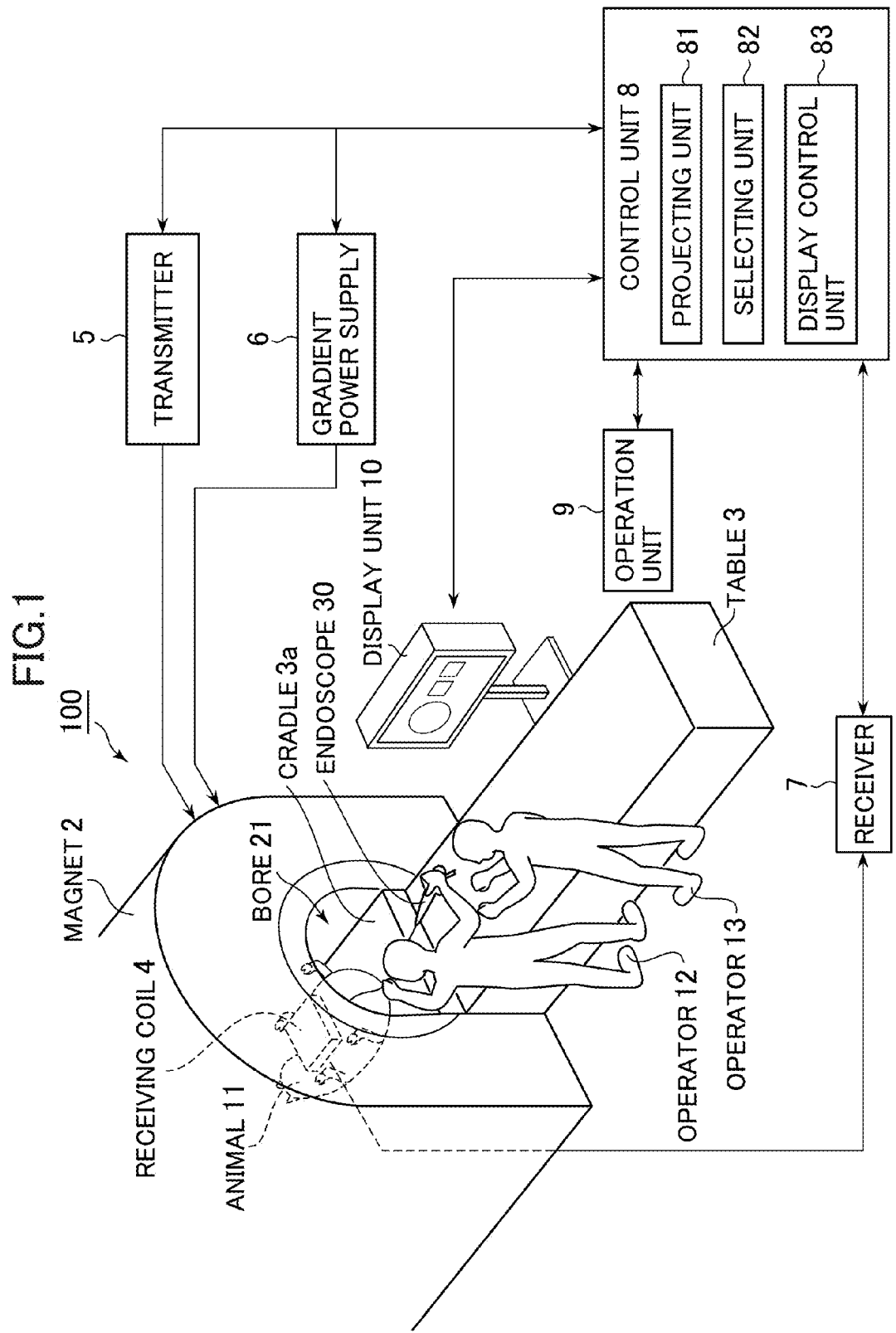

ENDOSCOPE 30

DISTAL END OF ENDOSCOPE 30

MAGNETIC SENSOR 33
LIGHT SOURCE 31
OPTICAL FIBER 32
DISTAL END OF ENDOSCOPE 30
LIGHT SOURCE 31
SURGICAL INSTRUMENT 34

FIG.4
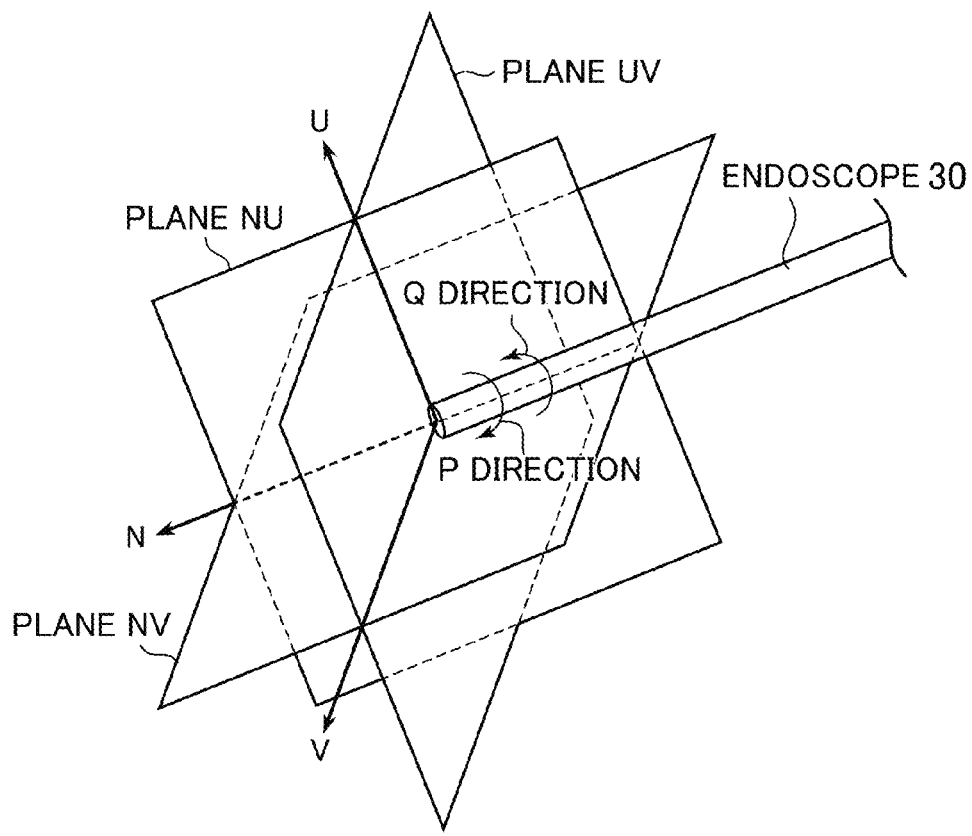
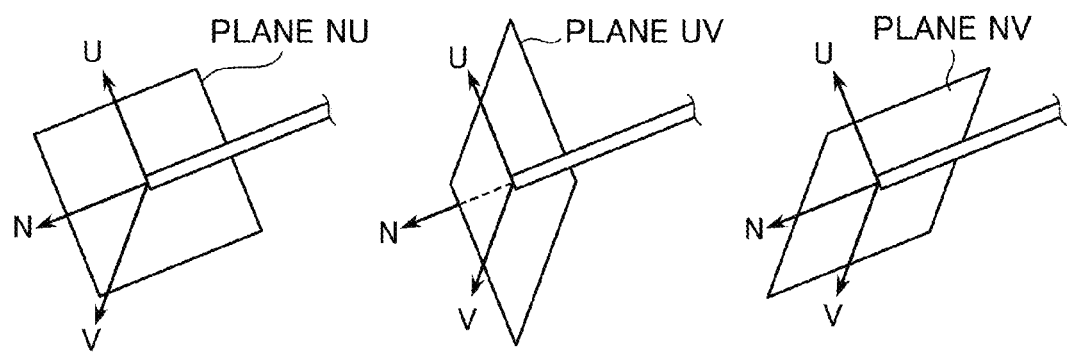

ROTATE ENDOSCOPIC IMAGE CLOCKWISE BY $\alpha = \alpha_0$ ABOUT ORIGIN $O_2$

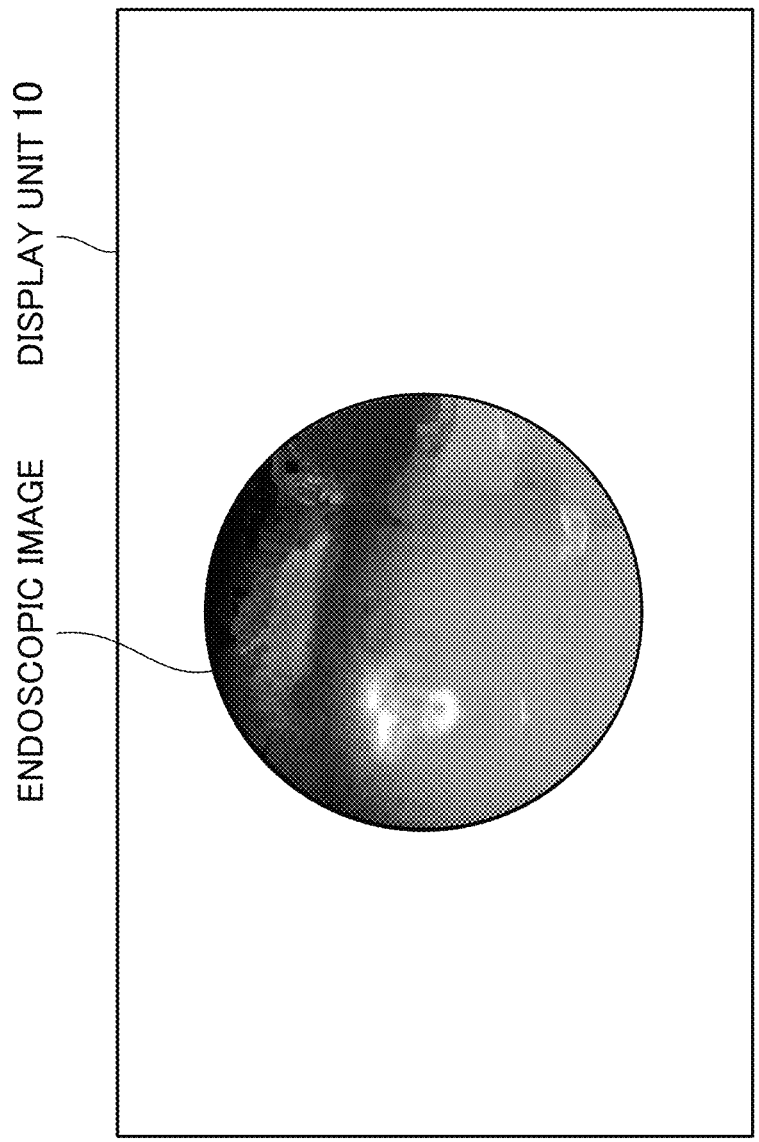

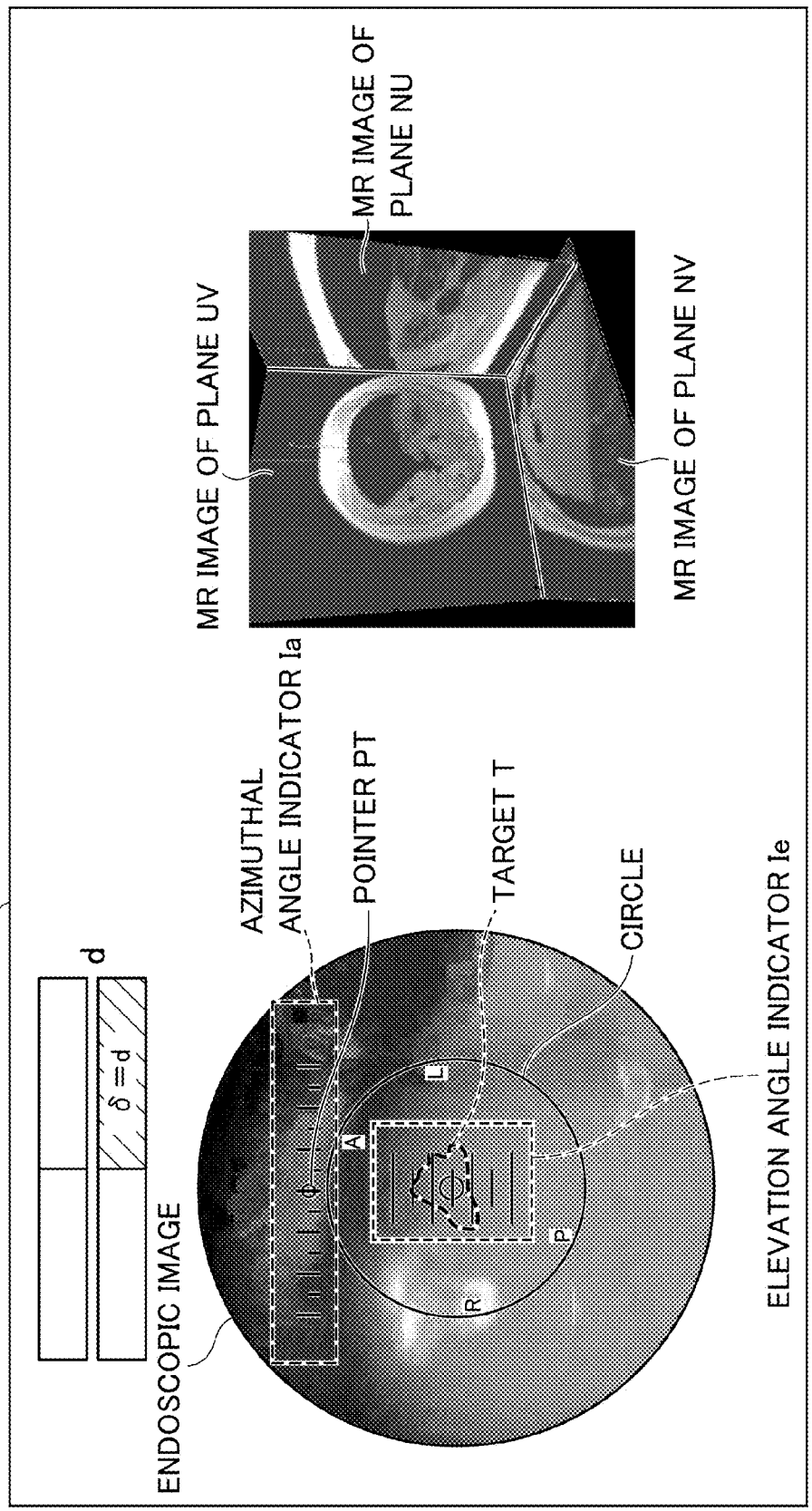

DISPLAY DEVICE, MEDICAL DEVICE, DISPLAY METHOD AND PROGRAM

CROSS REFERENCE TO RELATED APPLICATIONS

This application is a National Stage Entry of PCT/JP2013/077928 filed Oct. 15, 2013, which claims priority to Japanese Patent Application No. 2012-0233156 filed Oct. 22, 2012, which is hereby incorporated by reference in its entirety.

BACKGROUND

The present invention relates to a display device which displays an endoscopic image, a medical apparatus having the display device, a display method for displaying the endoscopic image, and a program used in the display device.

There has recently been known a method to image a patient by a medical apparatus (MR apparatus, CT apparatus, etc.) while observing the body of the patient by an endoscope, and perform surgery while viewing an endoscopic image and medical images (MR images and CT images) (refer to, for example, Japanese Patent Application Laid-Open No. 2009-172050).

However, since the visual field of the endoscope is generally narrow, the range in which an operator is able to make visual recognition through an endoscopic image is limited. Thus, the operator needs to determine the direction of movement of the endoscope, etc. under the condition on which the visible range is limited, and undergoes a large burden. For this reason, it has been desired to reduce a burden on the operator who manipulates the endoscope.

BRIEF DESCRIPTION

In a first aspect, a display device displaying an endoscopic image obtained by an endoscope for observing an object is provided. The display device includes a projecting unit configured to project coordinate axes set to the object onto the endoscopic image, and a display unit configured to display thereon the endoscopic image and the coordinate axes projected onto the endoscopic image.

In a second aspect, a medical apparatus having the display device according to the first aspect is provided.

In a third aspect, a display method for displaying an endoscopic image obtained by an endoscope for observing an object is provided. The method includes projecting coordinate axes set to the object onto the endoscopic image, and displaying the endoscopic image and the coordinate axes projected onto the endoscopic image.

In a fourth aspect, a program for a display device having a display unit configured to display an endoscopic image obtained by an endoscope for observing an object is provided. The program allows a computer to execute a projection process for projecting coordinate axes set to the object onto the endoscopic image, and a display control process for allowing the display unit to display the endoscopic image and the coordinate axes projected onto the endoscopic image.

Coordinate axes projected onto an endoscopic image are displayed on a display unit. Thus, an operator is able to easily recognize the correspondence between a portion displayed on the endoscopic image and the coordinate axes.

BRIEF DESCRIPTION OF THE DRAWINGS

FIG. 1 is a schematic diagram of a magnetic resonance apparatus of a first embodiment.

FIG. 4 is an explanatory diagram of vectors defined with respect to the endoscope.

FIG. 9 is a diagram schematically showing one example of the endoscopic image displayed on the display unit.

FIG. 51 is a diagram showing one example in which the MR image of the plane UV, the MR image of the plane NU and the MR image of the plane NV are displayed.

DETAILED DESCRIPTION

Figure 2A:
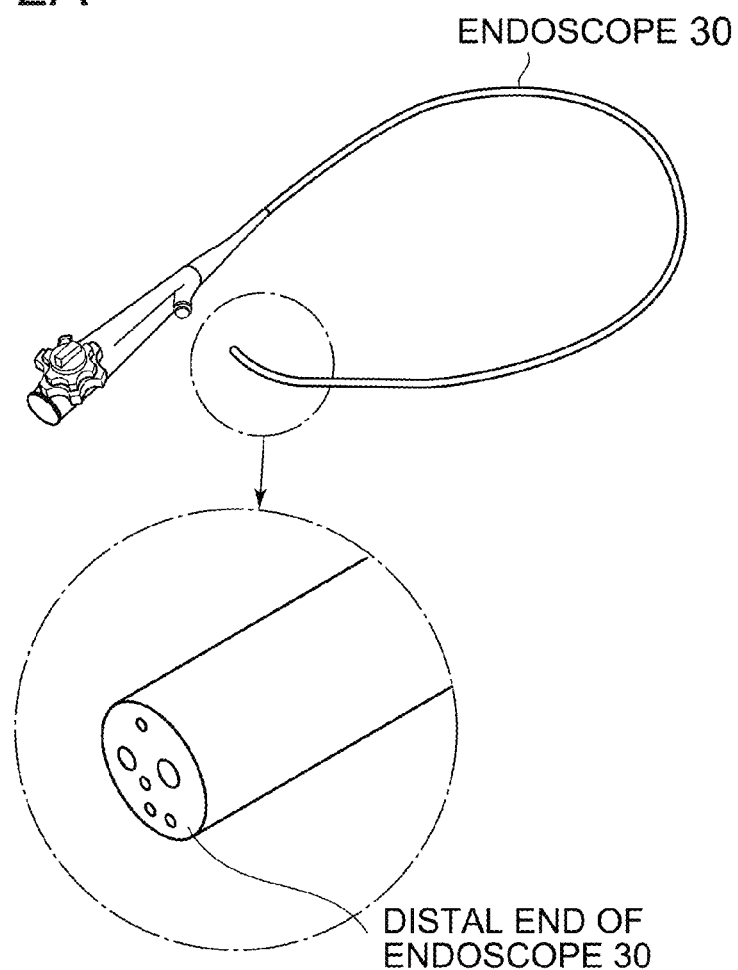
FIGS. 2A and 2B are an explanatory diagram of the structure of an endoscope.

Although exemplary embodiments will hereinafter be described, the disclosure is not limited to the following embodiments.

(1) First Embodiment

FIG. 1 is a schematic diagram of a magnetic resonance apparatus of a first embodiment.

The magnetic resonance apparatus (hereinafter referred to as an "MR apparatus" and MR: Magnetic Resonance) 100 has a magnet 2, a table 3, a receiving coil 4, etc.

The magnet 2 has a bore 21. Further, a superconductive coil, a gradient coil, an RF coil, etc. are built in the magnet 2. The superconductive coil applies a static magnetic field, the gradient coil applies a gradient magnetic field, and the RF coil transmits RF pulses.

The table 3 has a cradle 3a. The cradle 3a is configured to be movable in the bore 21. An animal 11 which is to undergo surgery has been laid on the cradle 3a. An endoscope 30 has been inserted into the animal 11. Operators 12 and 13 perform surgery of the animal 11 while operating the endoscope 30.

The receiving coil 4 is attached to the animal 11. The receiving coil 4 receives magnetic resonance signals from the animal 11.

The MR apparatus 100 further includes a transmitter 5, a gradient power supply 6, a receiver 7, a control unit 9, an operation unit 9 and a display unit 10, etc.

The transmitter 5 supplies a current to the RF coil, and the gradient power supply 6 supplies a current to the gradient coil.

The receiver 7 performs signal processing (for example, detection) on each signal received from the receiving coil 4.

The control unit 8 controls the operation of each unit of the MR apparatus 100 so as to implement various operations of the MR apparatus 100, such as reconstructing an image, based on data received from the receiver 7. The control unit 8 has a projecting unit 81, a selecting unit 82 and a display control unit 83, etc.

The projecting unit 81 projects coordinate axes AP, RL and SI (refer to, for example, FIGS. 6A and 6B) onto an endoscopic image obtained by the endoscope 30.

The selecting unit 82 selects the coordinate axis to be displayed in superposition on the endoscopic image from among the coordinate axes AP, RL and SI.

The display control unit 83 controls the display unit 10.

The control unit 8 is one example which configures the projecting unit 81, the selecting unit 82 and the display control unit 83 and functions as these units by executing a predetermined program.

The operation unit 9 is operated by the operator and inputs various information to the control unit 8. The display unit 10 displays the endoscopic image obtained by the endoscope 30, etc. Incidentally, a combination of the display unit 10 and the control unit 8 is one example of a display device.

The MR apparatus 100 is configured as described above.

The endoscope 30 will next be described.

Figure 2B:
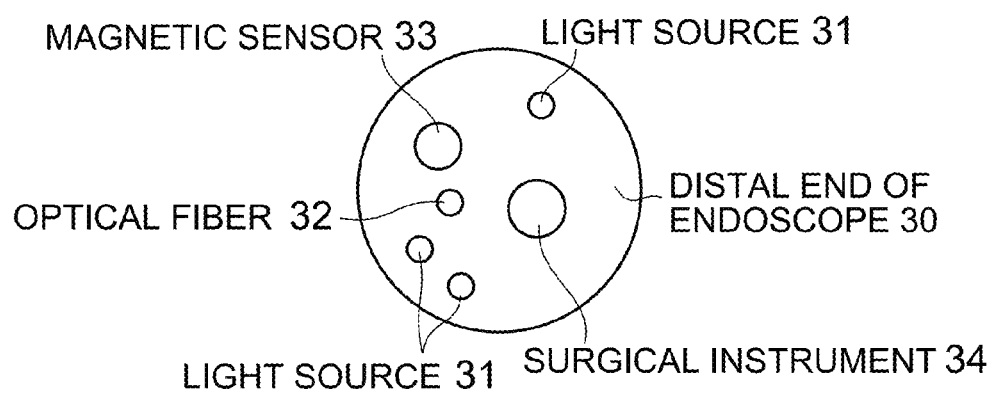

FIGS. 2A and 2B are an explanatory diagram of the structure of the endoscope 30.

FIG. 2A is an external diagram of the endoscope 30, and FIG. 2B is a front diagram the distal end of the endoscope 30.

Figure 3:
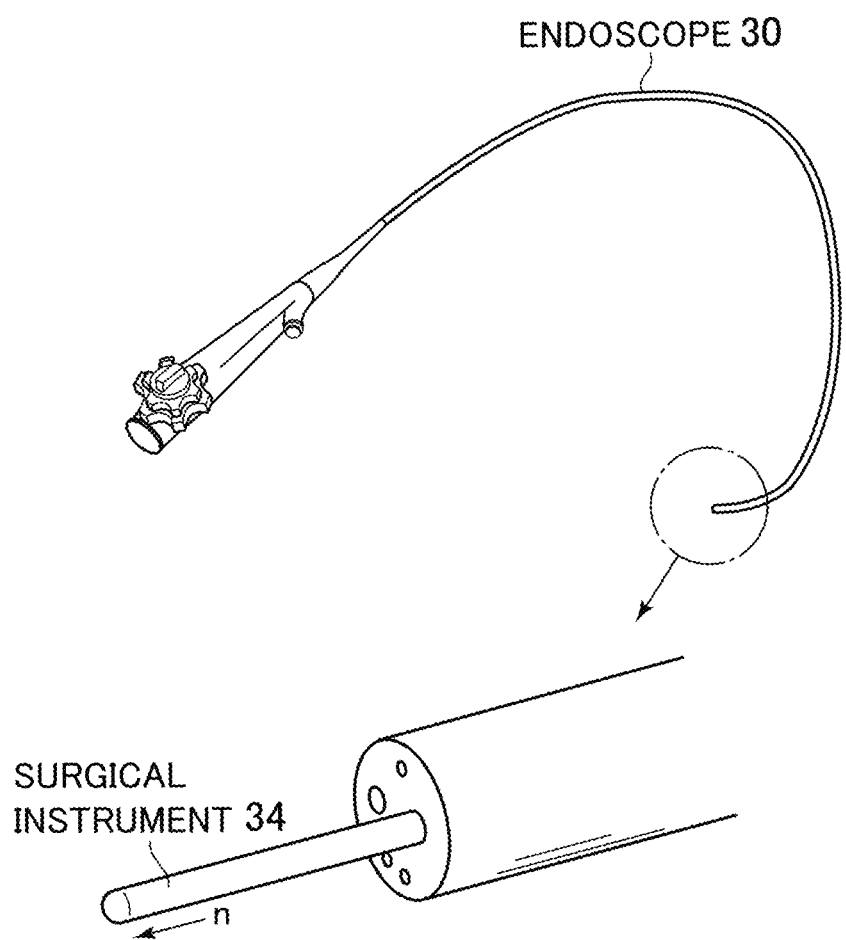
FIG. 3 is a diagram showing a situation in which the surgical instrument is protruded from the distal end of the endoscope.

The endoscope 30 is provided with a light source 31, an optical fiber 32, a magnetic sensor 33 and a surgical instrument 34, etc. The magnetic sensor 33 detects a gradient magnetic field and determines the position of the distal end of the endoscope 30 and the orientation of the distal end of the endoscope 30. The surgical instrument 34 is a tool for performing surgical treatment of the animal 11 and is configured such that it can be protruded from the distal end of the endoscope 30. FIG. 3 is a diagram showing a situation in which the surgical instrument 34 is protruded from the distal end of the endoscope 30. The operator is able to protrude the surgical instrument 34 in a predetermined direction n from the distal end of the endoscope 30 by operating an operation unit of the endoscope 30.

Figure 5A:
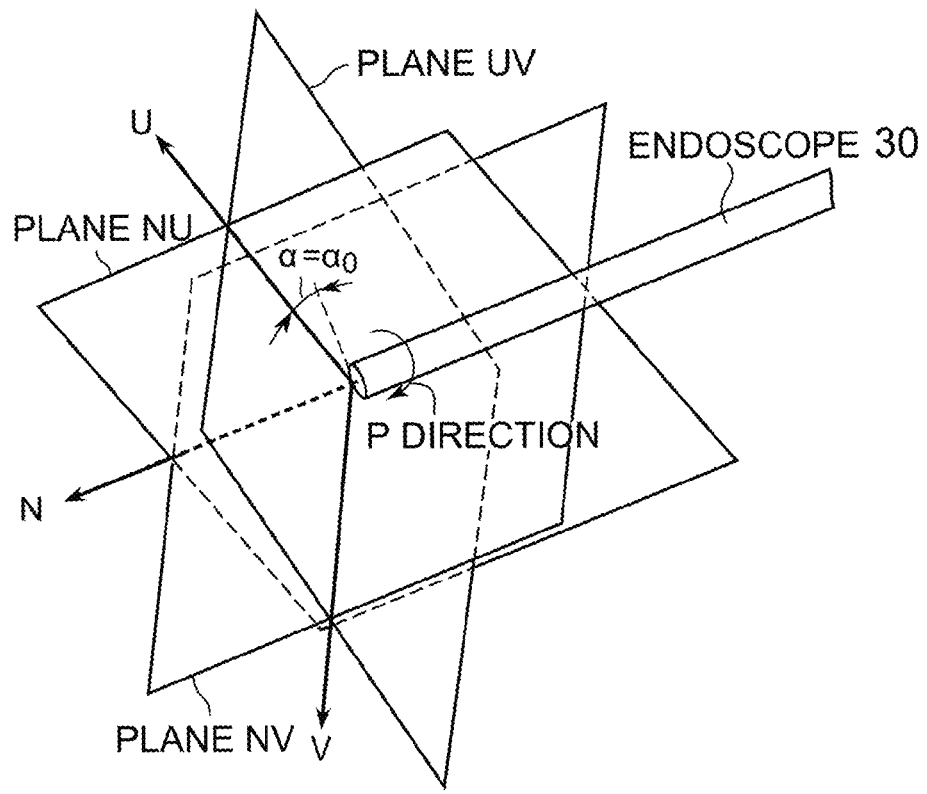
FIGS. 5A and 5B are a diagram showing the planes NV, NU and UV in the case where the distal end of the endoscope is rotated.
Figure 5B:
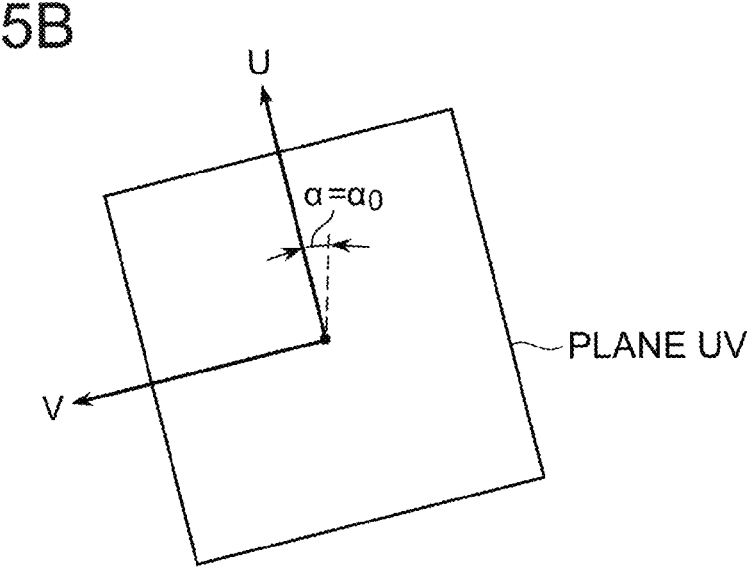

Further, vectors have been defined in the endoscope 30 (refer to FIGS. 4 and 5A and 5B).

FIG. 4 is an explanatory diagram of the vectors defined with respect to the endoscope 30.

The three vectors: vector N, vector U and vector V have been defined at the distal end of the endoscope 30. The vectors N, U and V are vectors perpendicular to each other. The direction of the vector N is set in a protruding direction n (refer to FIG. 3) of the surgical instrument 34 of the endoscope 30. Three planes NV, NU and UV have been defined by the vectors N, U and V. These planes NV, NU and UV are respectively planes defined as follows:

Plane NV: plane defined by vectors N and V,
Plane NU: plane defined by vectors N and U, and
Plane UV: plane defined by vectors U and V.

The distal end of the endoscope 30 is configured to be capable of being rotated in P and Q directions with the vector N as the central axis. FIGS. 5A and 5B are a diagram showing the planes NV, NU and UV in the case where the distal end of the endoscope 30 is rotated.

FIG. 5A is a diagram showing the planes NV, NU and UV in the case where the distal end of the endoscope 30 is rotated by an angle $\alpha=\alpha 0$ in the P direction about the vector N, and FIG. 5B is a diagram in the case where FIG. 5A is viewed from the direction of the vector N.

By rotating the distal end of the endoscope 30 in the P direction (or Q direction), the planes NV, NU and UV can also be rotated about the vector N.

The MR apparatus 100 can execute the following scans during the surgery:

(1) Scan A for acquiring MR image of plane NV,
(2) Scan B for acquiring MR image of plane NU, and
(3) Scan C for acquiring MR image of plane UV.

The operators 12 and 13 can optionally select the MR image displayed on the display unit 10 from among the MR image acquired by the scan A, the MR image acquired by the scan B and the MR image acquired by the scan C.

A description will hereinafter be made about a procedure by which the operators 12 and 13 perform surgery on the animal 11 using the endoscope 30.

Figure 6A:
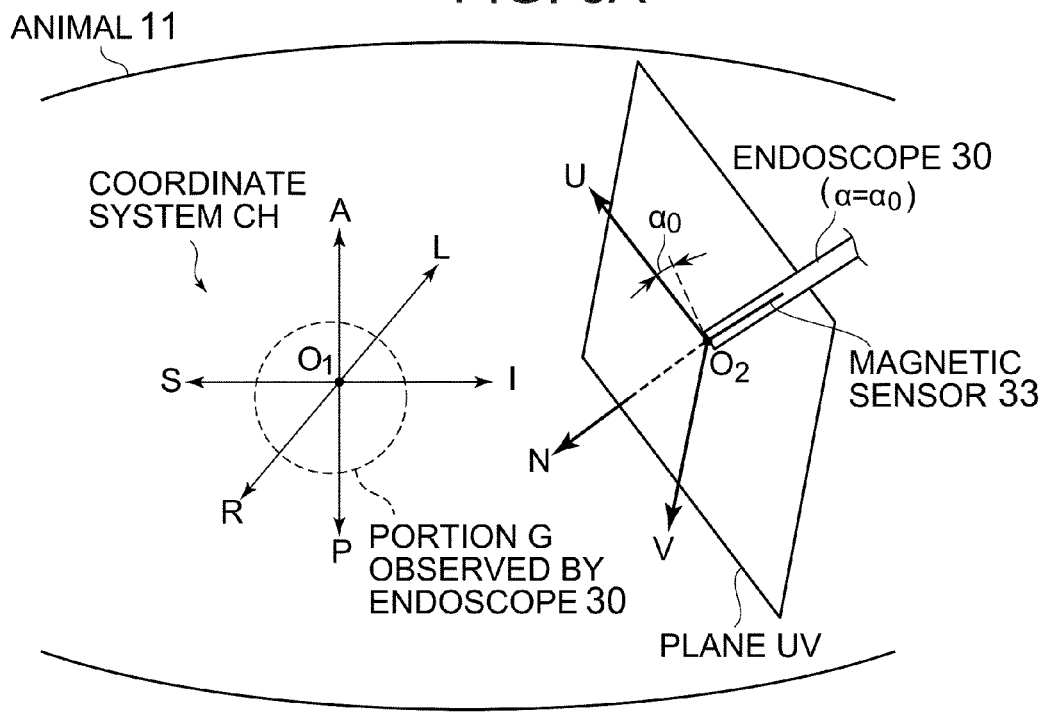
FIGS. 6A and 6B are a diagram schematically showing the manner when the endoscope is inserted into an animal.
Figure 6B:
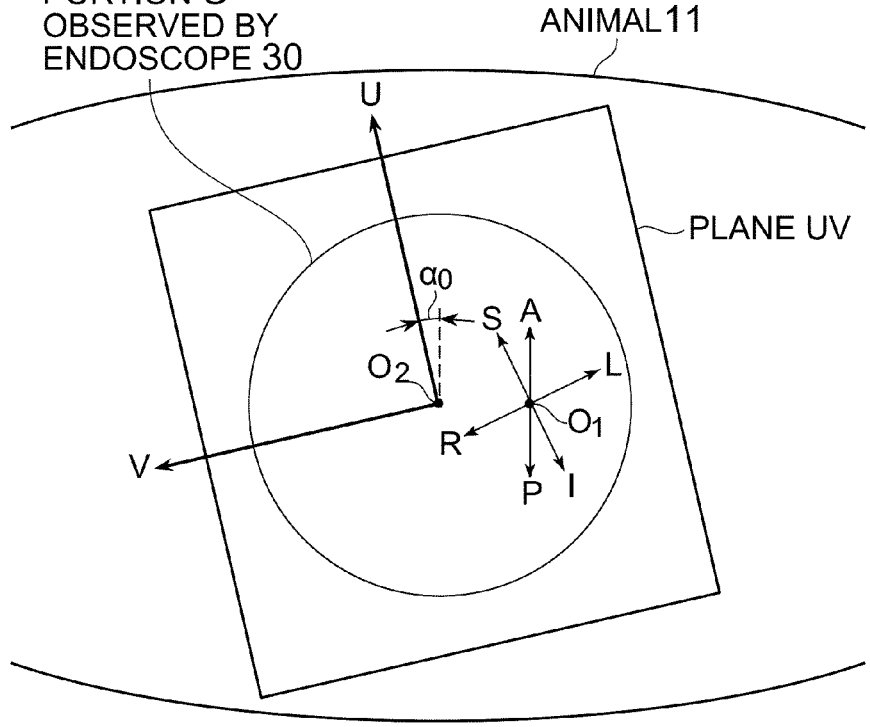

FIGS. 6A and 6B are a diagram schematically showing a situation in which the endoscope 30 is inserted into the animal 11.

FIG. 6A is a diagram showing a positional relationship between a coordinate system CH set to the animal 11 and the vectors N, U and V of the endoscope 30, and FIG. 6B is a diagram in the case where FIG. 6A is viewed from the direction of the vector N. There is shown in FIGS. 6A and 6B, an example where the rotational angle α of the distal end of the endoscope 30 is $\alpha=\alpha_0$.

The coordinate system CH (coordinate axes AP, RL and SI) are set to the animal 11. The origin $O_1$ of the coordinate axes AP, RL and SI is positioned in the isocenter of the magnet 2, for example.

The magnetic sensor 33 of the endoscope 30 detects a gradient magnetic field. The gradient magnetic field detected by the magnetic sensor 33 is transmitted to the control unit 8. The control unit 8 detects the position of the distal end of the endoscope 30 and the orientation of the distal end of the endoscope 30 on the basis of the gradient magnetic field detected by the magnetic sensor 33. By detecting the position and orientation of the distal end of the endoscope 30, the positions and orientations of the vectors N, U and V can be detected.

A portion G, which is observed by the endoscope 30, is schematically illustrated in FIGS. 6A and 6B. The portion G observed by the endoscope 30 is obtained as an endoscopic image.

Figure 7A:
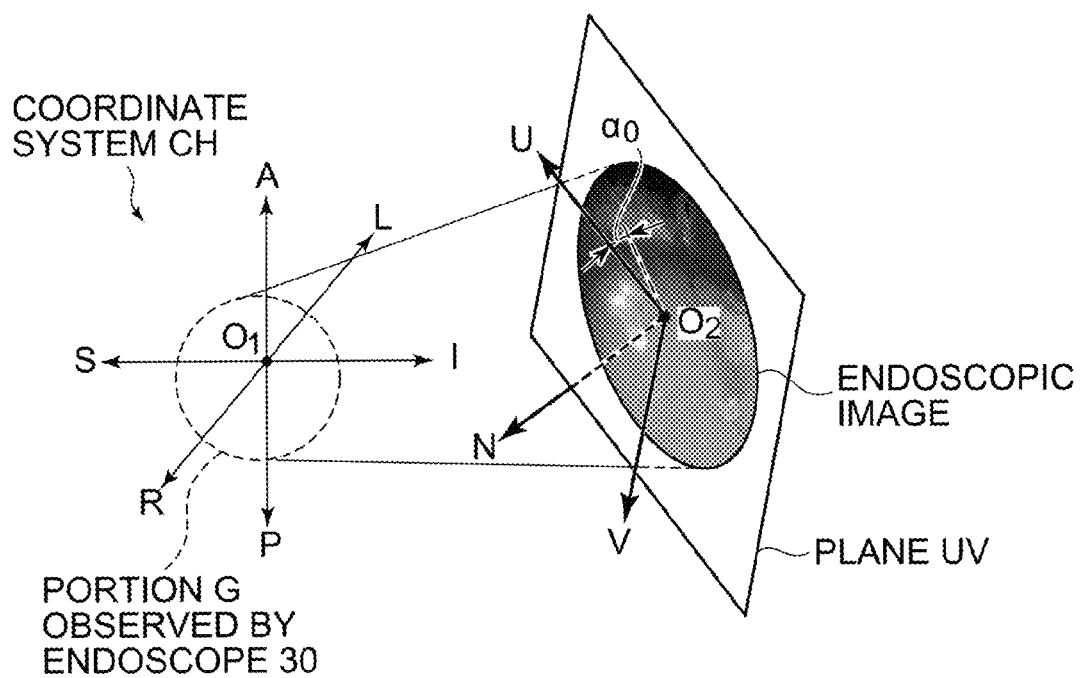
FIGS. 7A and 7B are an explanatory diagram of an endoscopic image.
Figure 7B:
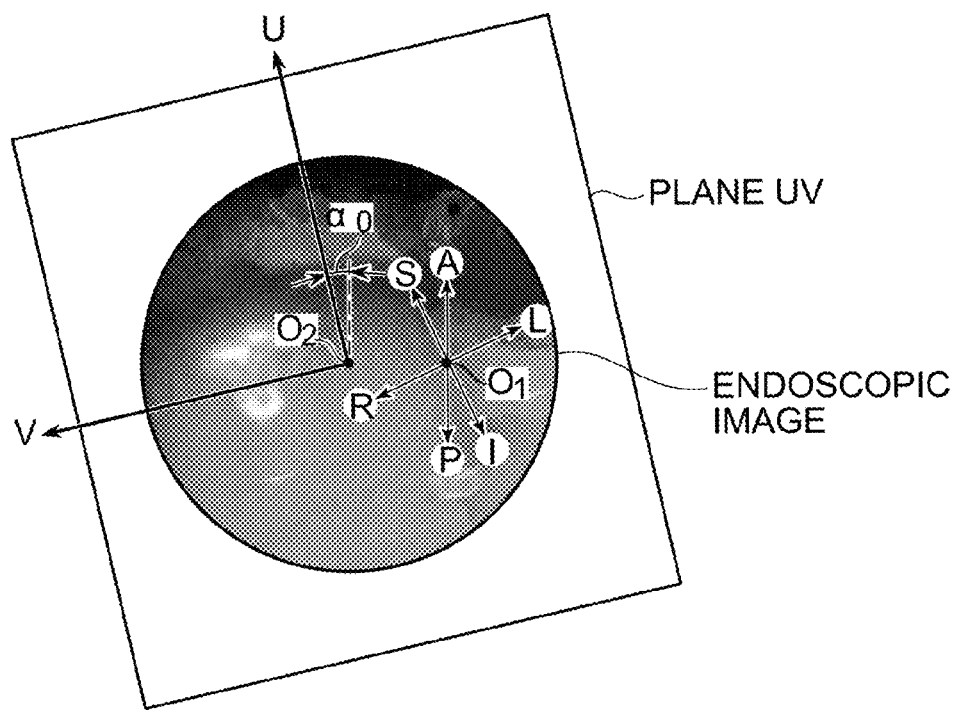

FIGS. 7A and 7B are an explanatory diagram of the endoscopic image.

As illustrated in FIG. 7A, the endoscopic image can be obtained as an image which is obtained by projecting the portion G observed by the endoscope 30 onto the plane UV. The vector U defines the upper side of the endoscopic image and the vector V defines the left side of the endoscopic image. There is shown in FIG. 7B, a diagram in the case where FIG. 7A is viewed from the direction of the vector N. Since the distal end of the endoscope 30 is rotated by $\alpha=\alpha_0$ (refer to FIGS. 6A and 6B), the endoscopic image is also inclined by $\alpha=\alpha_0$. The endoscopic image is displayed on the display unit 10 (refer to FIG. 1) by the display control unit 83.

Figure 8A:
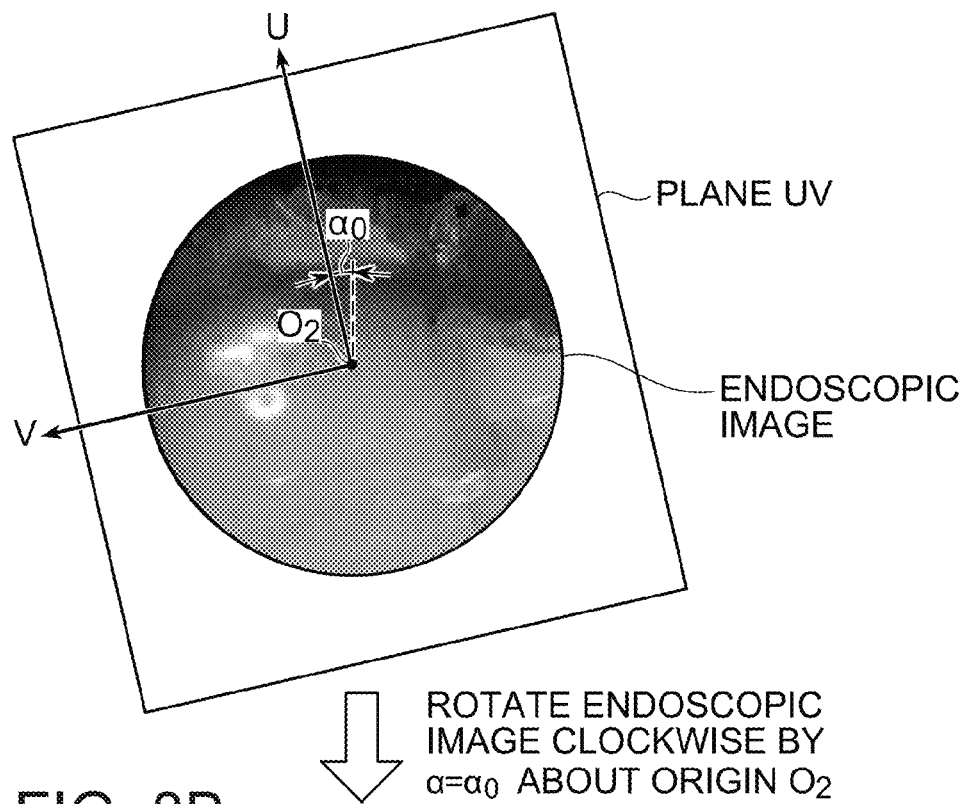
FIGS. 8A and 8B are a diagram for explaining a way of displaying the endoscopic image on the display unit.
Figure 8B:
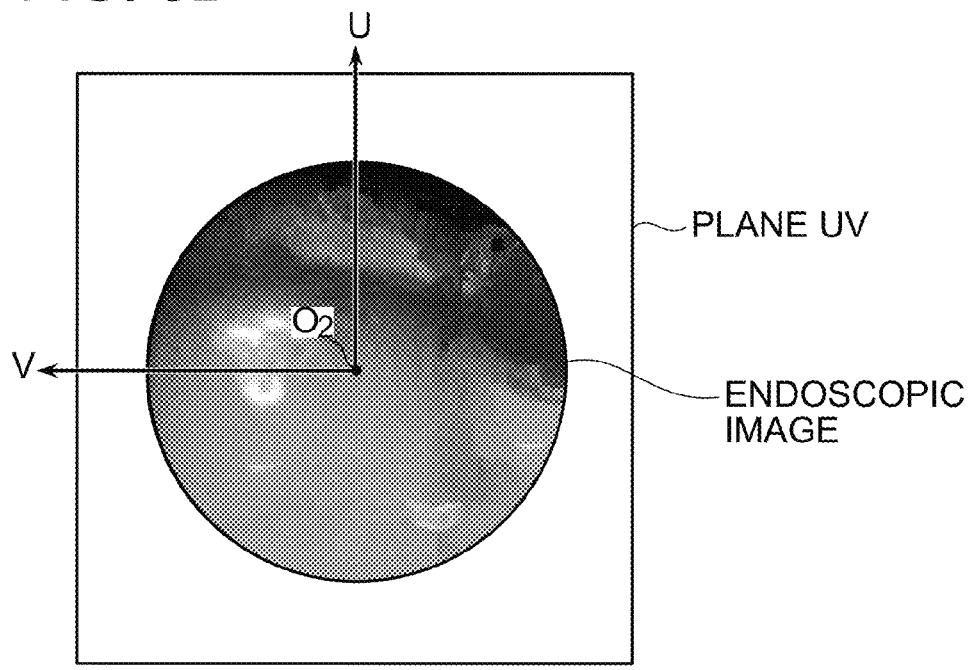

FIGS. 8A and 8B are a diagram for explaining a way of displaying the endoscopic image on the display unit 10.

When the distal end of the endoscope 30 is being rotated by $\alpha=\alpha 0$, the resultant endoscopic image is also rotated by $\alpha=\alpha_0$ (refer to FIG. 8A). Therefore, in order to restore the rotational angle of the endoscopic image, the endoscopic image is rotated by $\alpha 0$ in a clockwise direction about its origin O2 (refer to FIG. 8B). Thus, the vector U can be turned to the upper side, and the vector V can be turned to the left side. After the endoscopic image has been rotated in this way, the endoscopic image is displayed on the display unit 10. FIG. 9 schematically shows one example of the endoscopic image displayed on the display unit 10. Regardless of the rotational angle of the distal end of the endoscope 30, the endoscopic image is displayed on the display unit such that the vector U is turned to the upper side.

Further, in the present embodiment, coordinate information of the coordinate system CH (coordinate axes AP, RL and SI) are also displayed on the display unit 10 in addition to the endoscopic image. A description will hereinafter be made about how the coordinate information is displayed.

FIGS. 10A, 10B, 11A, and 11B are diagrams for explaining a way of displaying the coordinate information of the coordinate system CH.

Figure 10A:
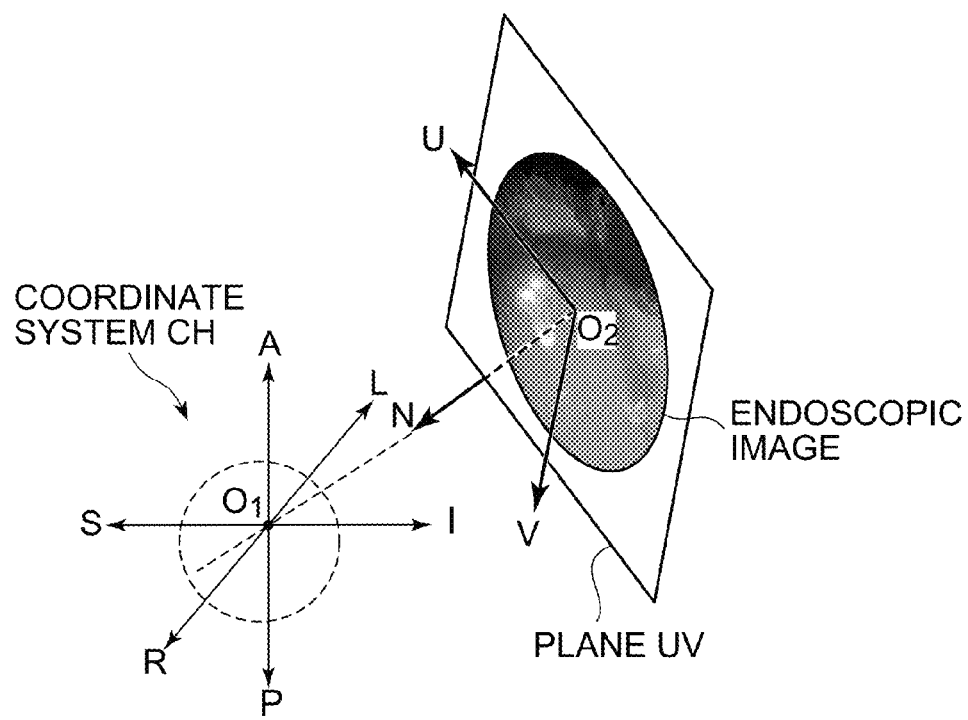
FIGS. 10A and 10B are a diagram for explaining a way of displaying the coordinate information of the coordinate system CH.
Figure 10B:
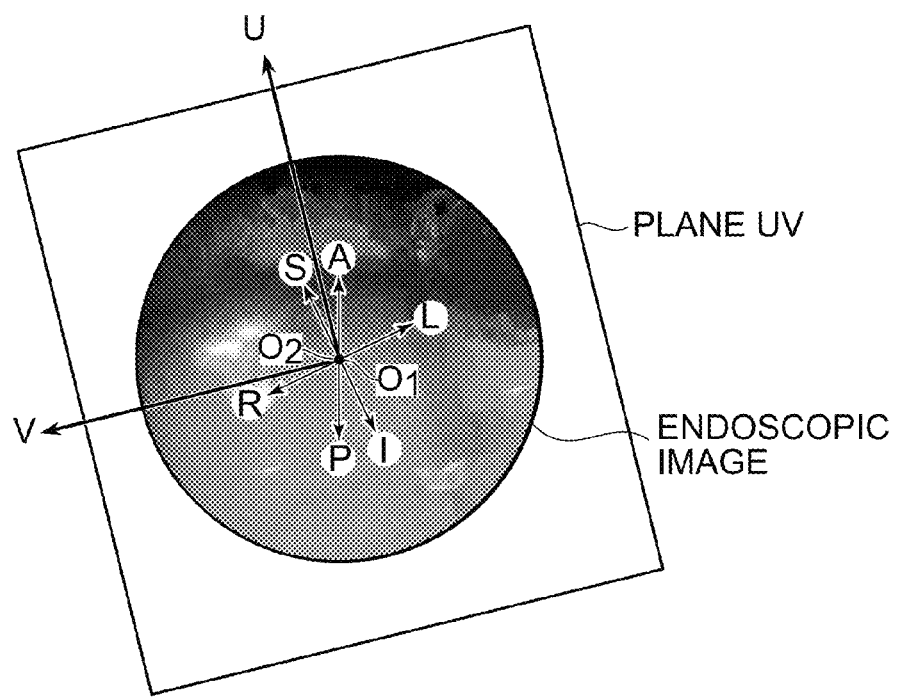

As shown in FIG. 10A, the projecting unit 81 (refer to FIG. 1) translates the vectors N, U and V in such a manner that the origin O1 of the coordinate system CH is positioned on an extension of the vector N. There is shown in FIG. 10B, a diagram in the case where FIG. 10A is viewed from the direction of the vector N. After the vectors N, U and V have been translated, the projecting unit 81 projects the coordinate axes AP, RL and SI onto the endoscopic image (refer to FIGS. 11A and 11B).

Figure 11A:
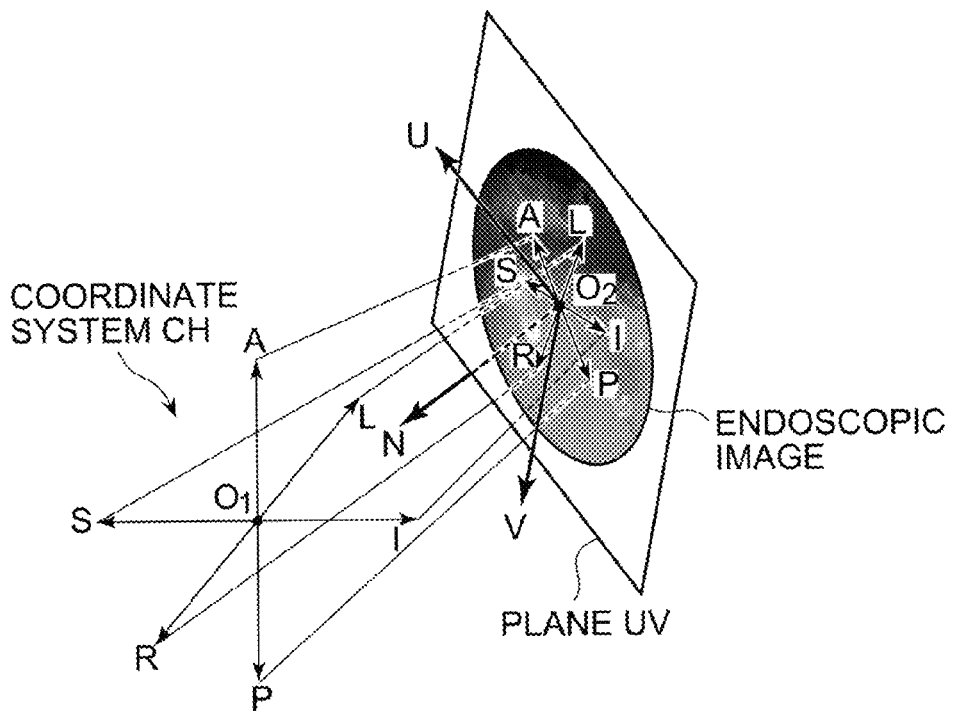
FIGS. 11A and 11B are a diagram showing the manner after coordinate axes AP, RL and SI are projected onto the endoscopic image.
Figure 11B:
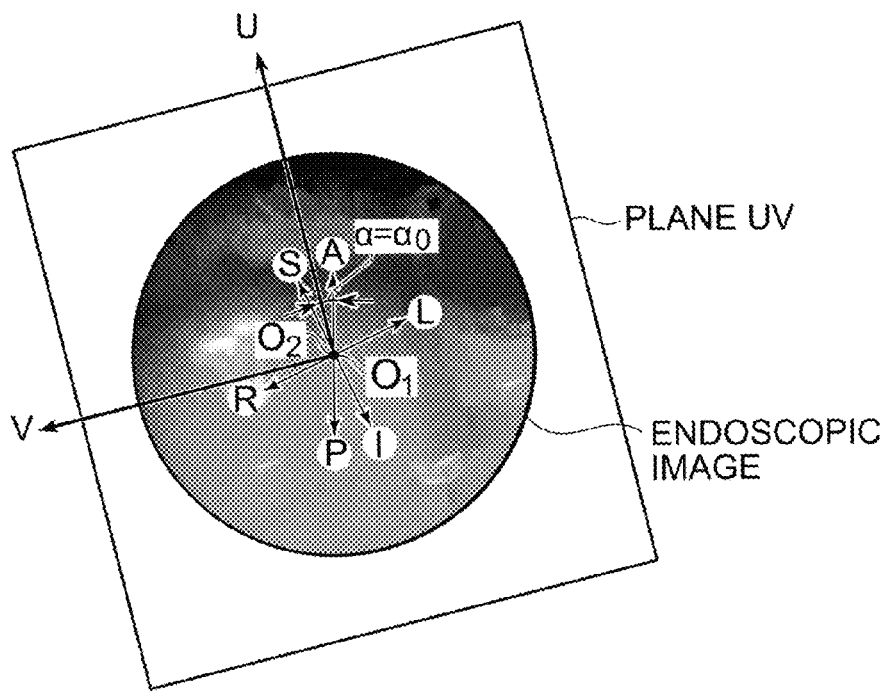

FIGS. 11A and 11B are a diagram showing the manner after the coordinate axes AP, RL and SI have been projected onto the endoscopic image. FIG. 11A is a diagram schematically showing a way of projecting the coordinate axes AP, RL and SI onto the endoscopic image, and FIG. 11B is a diagram in the case where FIG. 11A is viewed from the direction of the vector N.

By projecting the coordinate axes AP, RL and SI onto the endoscopic image, it is possible to obtain the correspondence between the coordinate axes AP, RL and SI and the portion displayed on the endoscopic image. The projected coordinate axes AP, RL and SI are displayed on the display unit 10 by the display control unit 83 together with the endoscopic image (refer to FIGS. 12A and 12B).

Figure 12A:
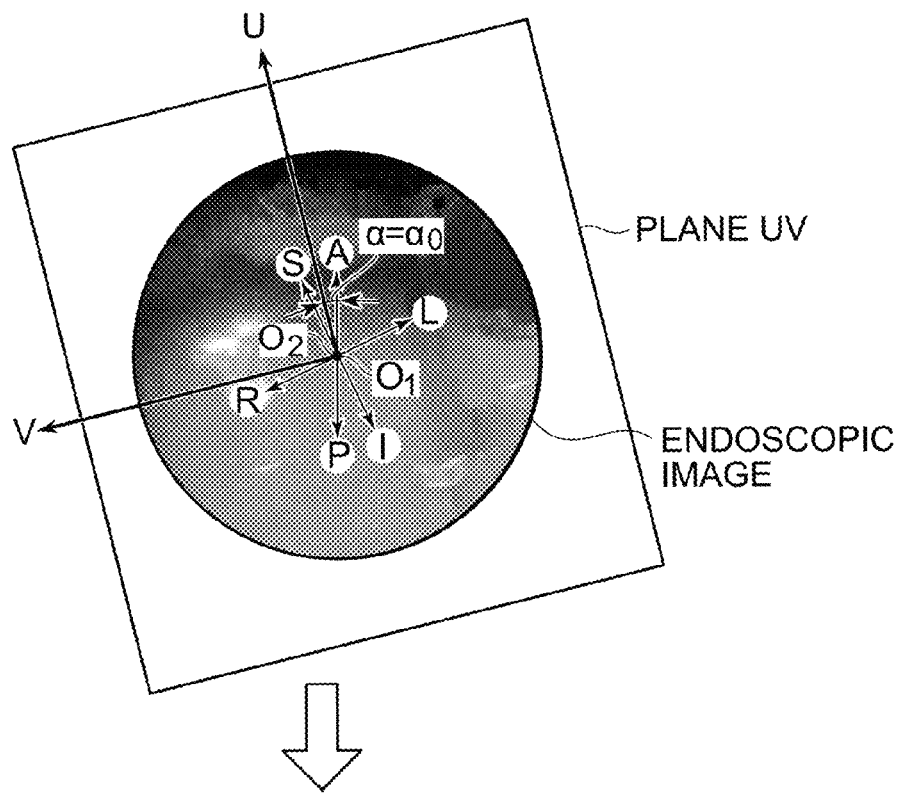
FIGS. 12A and 12B are a diagram for explaining a way of displaying the coordinate axes AP, RL and SI and the endoscopic image on the display unit.
Figure 12B:
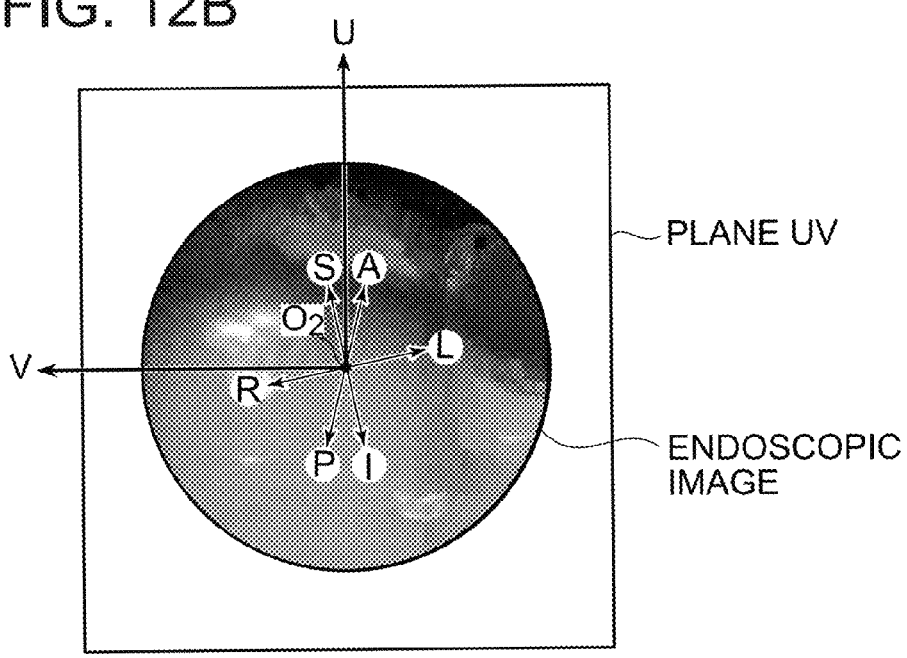

FIGS. 12A and 12B are a diagram for explaining a way of displaying the coordinate axes AP, RL and SI and the endoscopic image on the display unit 10.

Figure 13:
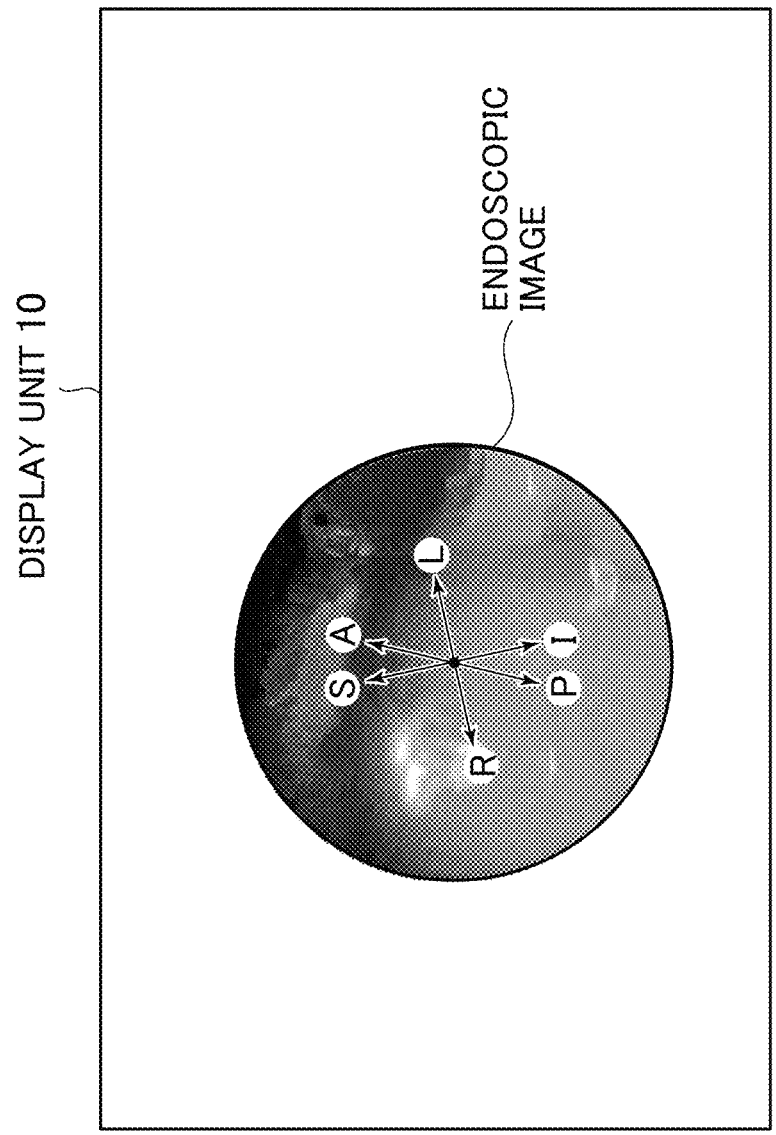
FIG. 13 is a diagram schematically showing one example of the endoscopic image displayed on the display unit.

Since the endoscopic image is being rotated by $\alpha=\alpha 0$ (refer to FIG. 12A), the endoscopic image is rotated clockwise by $\alpha 0$ about the origin O2 of the vector to restore the rotational angle of the endoscopic image (refer to FIG. 12B). Consequently, it is possible to turn the vector U to the upper side and turn the vector V to the left side. After the endoscopic image has been rotated in this way, the endoscopic image is displayed on the display unit 10. One example of the endoscopic image displayed on the display unit 10 is schematically illustrated in FIG. 13. Since the coordinate axes AP, RL and SI have been projected onto the endoscopic image, the operator is able to visually and easily recognize by simply looking at the endoscopic image, that the lower side of the endoscopic image is a P-axis side (belly side) and the upper side of the endoscopic image is an A-axis side (back side). Accordingly, the operator is able to use the information of the coordinate axes as a determination material for determining the direction of movement of the endoscope and the like. It is possible to reduce the burden on the operator.

Figure 14A:
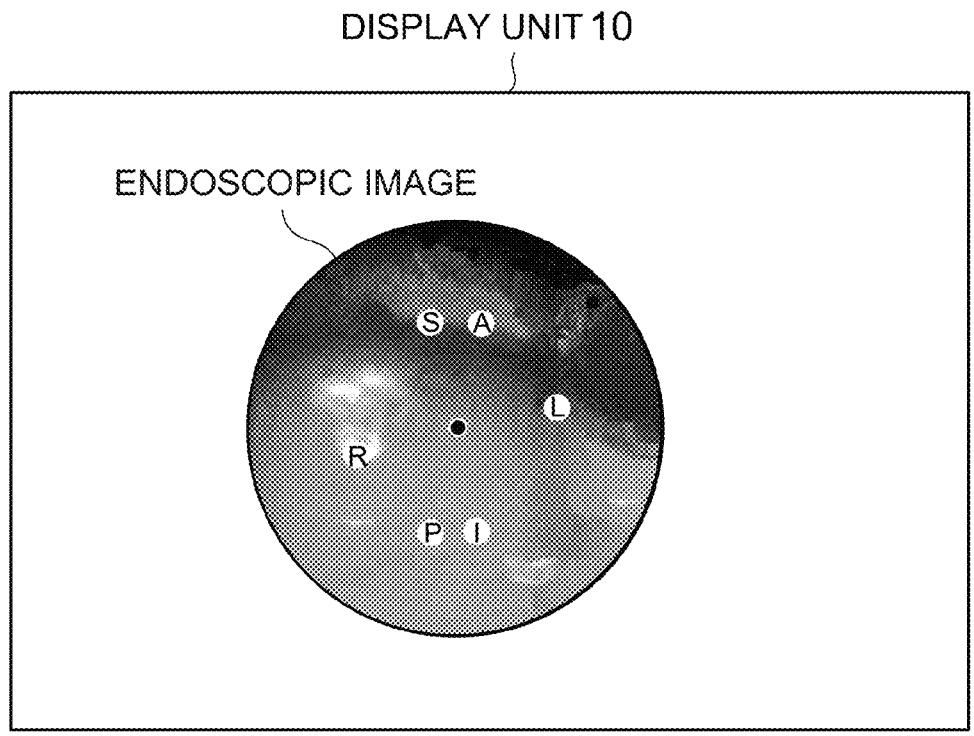
FIGS. 14A and 14B are a diagram showing an example of the endoscopic image displayed on the display unit.
Figure 14B:
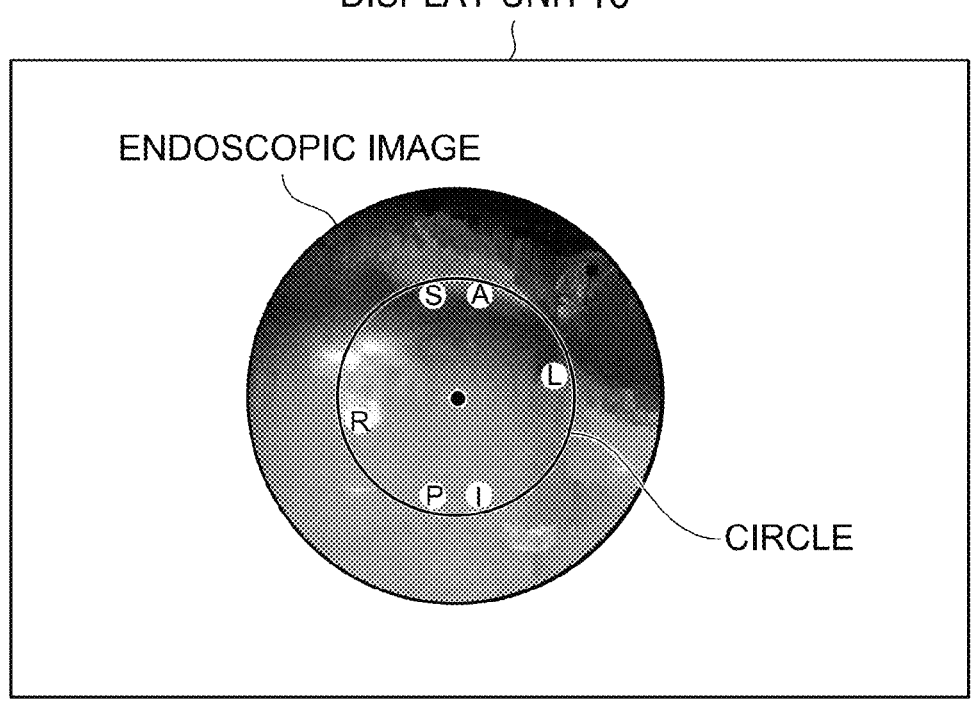

Incidentally, there are shown in FIG. 13, arrows which represent the coordinate axes AP, RL and SI. Since, however, these arrows overlap with the endoscopic image, the operator becomes a hindrance when visually identifying the endoscopic image. Therefore, when the endoscopic image is displayed on the display unit 10, these arrows are made invisible. FIGS. 14A and 14B show an example of the endoscopic image displayed on the display unit 10. In FIG. 14A, the arrows are not represented, and the alphabets "A" and "P" representing the AP axis, the alphabets "R" and "L" representing the RL axis and the alphabets "S" and "I" representing the SI axis are shown on the endoscopic image. Thus, it is possible to make the operator easier to see the endoscopic image.

On the other hand, in FIG. 14B, such a circle as to surround the alphabets "A", "P", "R", "L", "S" and "I" is added. By displaying this circle, it is possible to make it easy for the operator to visually recognize the position of a region of a central portion of the endoscopic image.

A description will next be made about how the AP axis, RL axis and SI axis change when the angle $\alpha$ of the distal end of the endoscope 30 is changed.

Figure 15A:
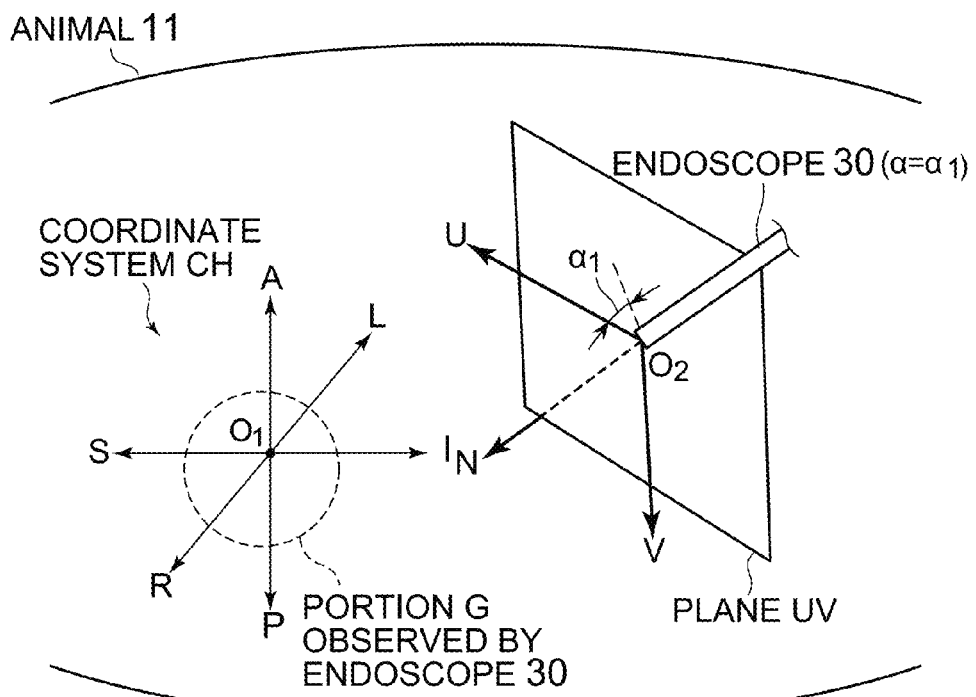
FIGS. 15A and 15B are a diagram showing a positional relationship between the coordinate system CH and the vectors N, U and V in the case where the rotational angle α of the distal end of the endoscope is changed from α0 to α1.
Figure 15B:
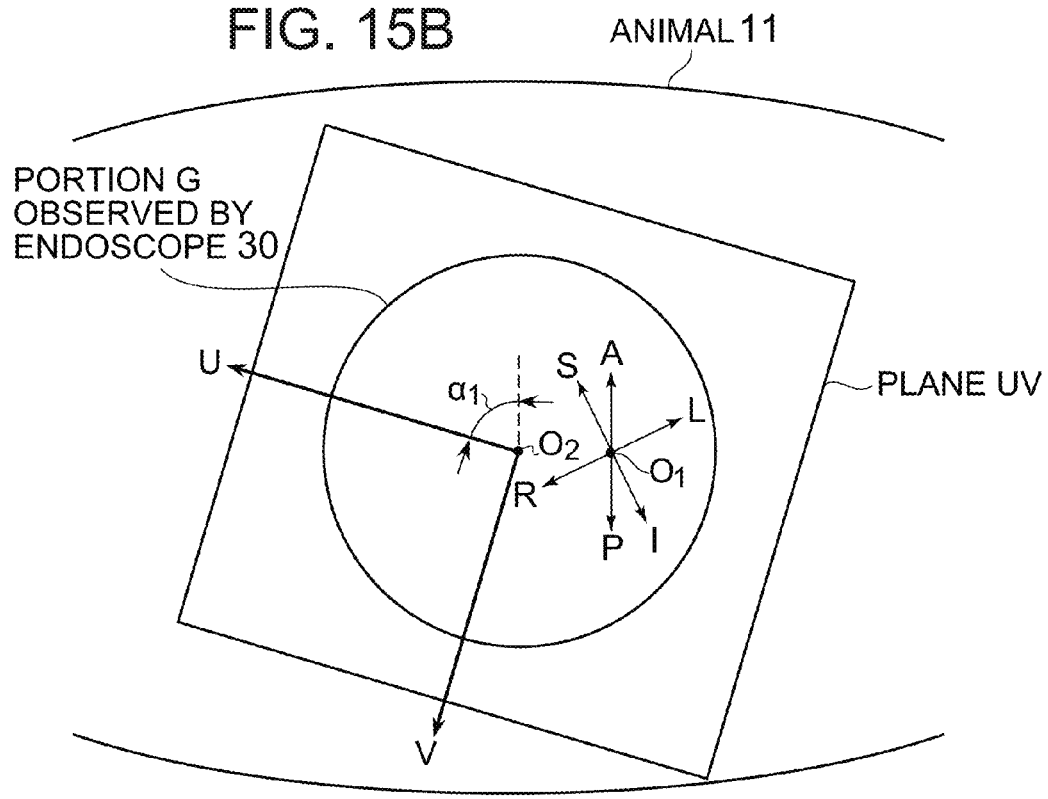
Figure 16A:
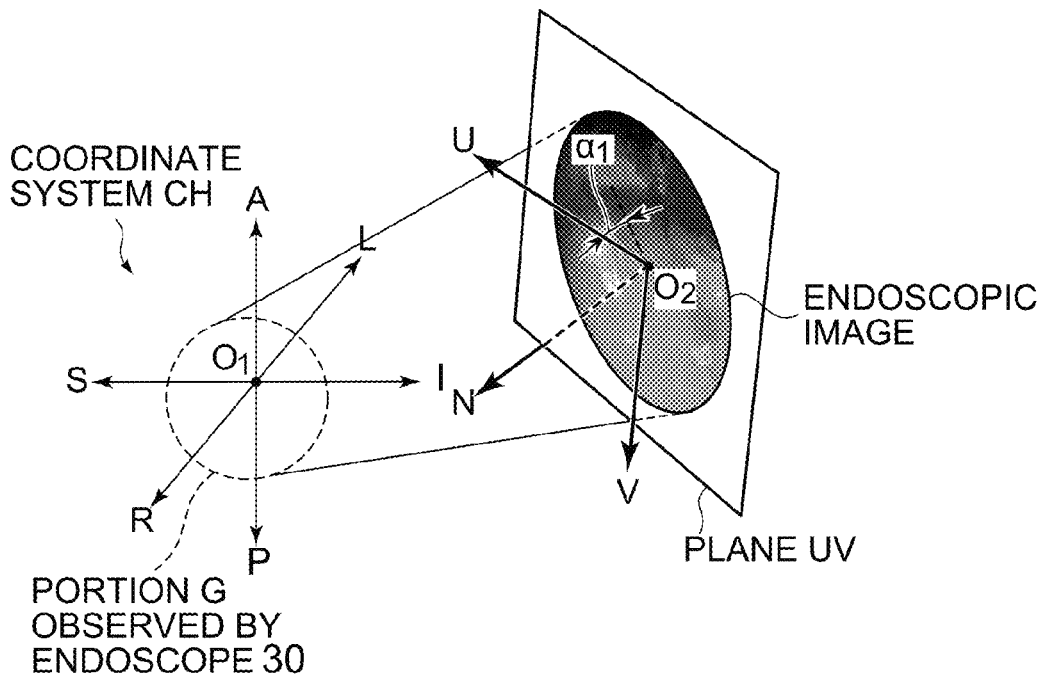
FIGS. 16A and 16B are an explanatory diagram of an endoscopic image obtained where α=α1.
Figure 16B:
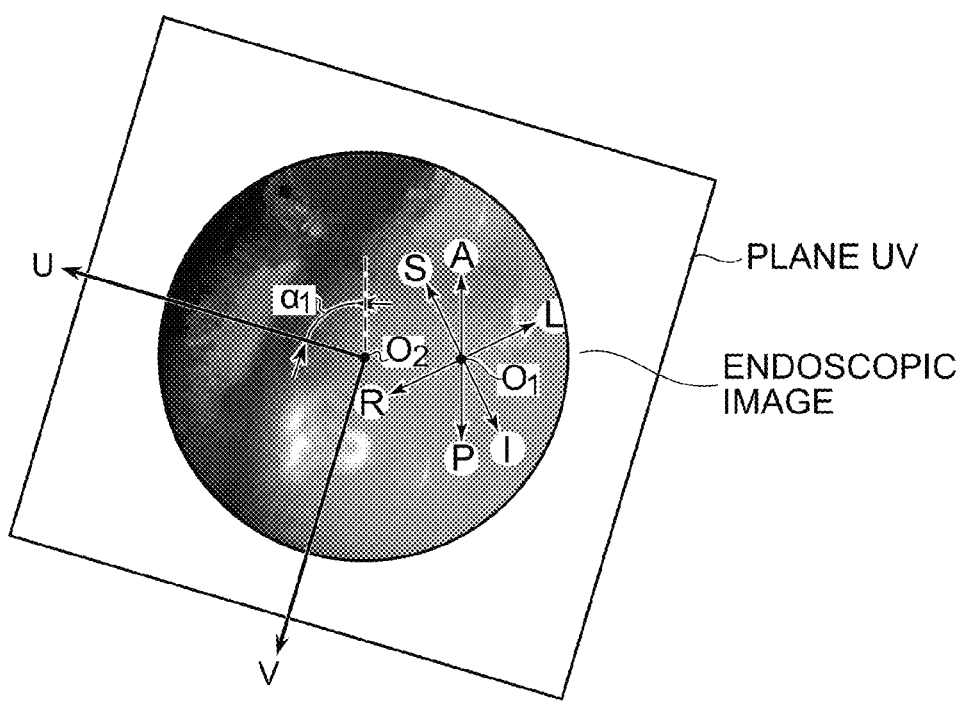

FIGS. 15A and 15B are a diagram showing a positional relationship between the coordinate system CH and the vectors N, U and V in the case where the rotational angle $\alpha$ of the distal end of the endoscope 30 is changed from $\alpha 0$ to $\alpha 1$, and FIGS. 16A and 16B are an explanatory diagram of the endoscopic image obtained where $\alpha=\alpha 1$.

Even if the rotational angle of the distal end of the endoscope 30 is changed, there is no change in portion G which is observed by the endoscope 30. Thus, as illustrated in FIG. 16A, an image which is obtained by projecting the portion G onto the plane UV is obtained as the endoscopic image even where $\alpha=\alpha 1$ as with the case where $\alpha=\alpha 0$. There is shown in FIG. 16B, a diagram in the case where FIG. 16A is viewed from the direction of the vector N.

Next, the coordinates axes AP, RL and SI are projected onto the endoscopic image (refer to FIGS. 17A, 17B, 18A, and 18B).

FIGS. 17A, 17B, 18A, and 18B are diagrams for explaining a way of projecting the coordinate axes AP, RL and SI onto the endoscopic image.

Figure 17A:
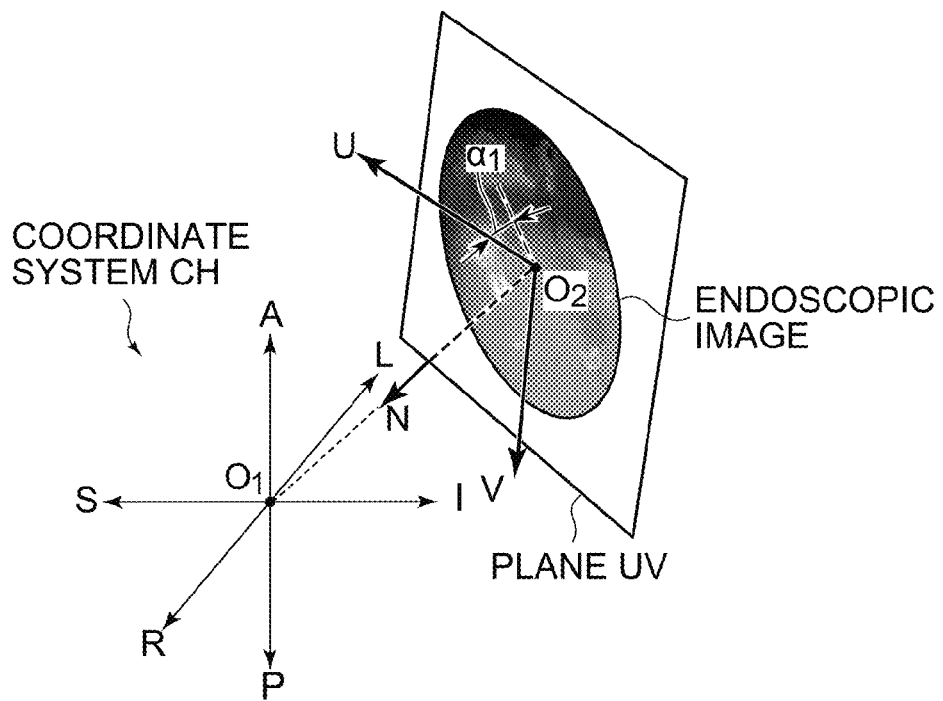
FIGS. 17A and 17B are a diagram for explaining a way of projecting the coordinate axes AP, RL and SI onto the endoscopic image.
Figure 17B:
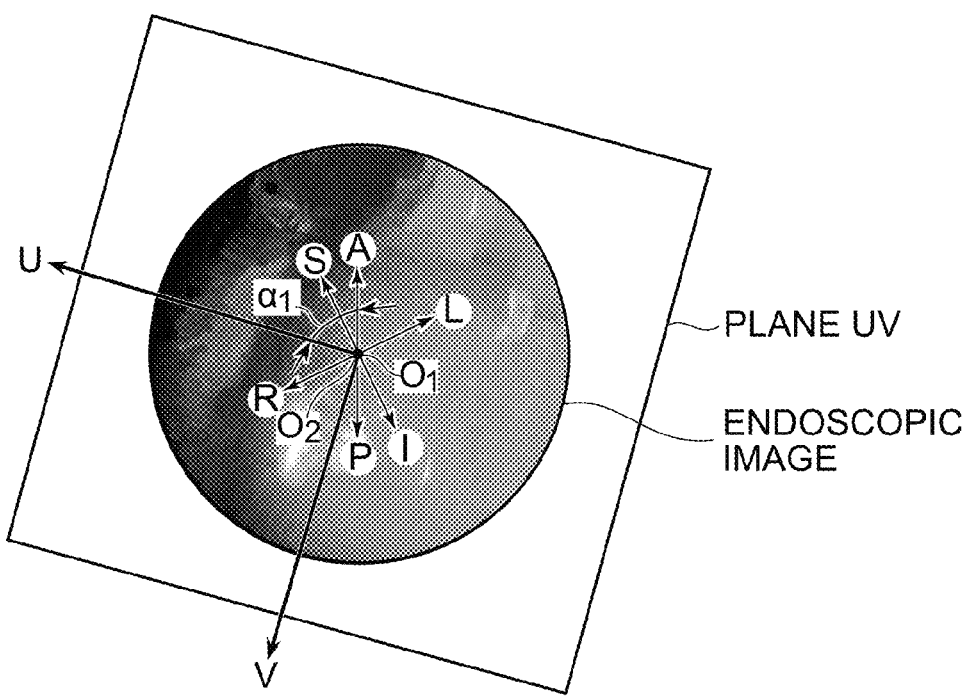

The projecting unit 81 first translates the vectors N, U and V in such a manner that the origin O1 of the coordinate system CH is positioned on an extension of the vector N as shown in FIG. 17A. There is shown in FIG. 17B, a diagram in the case where FIG. 17A is viewed from the direction of the vector N. After the vectors N, U and V have been translated, the projecting unit 81 projects the coordinate axes AP, RL and SI onto the endoscopic image (refer to FIGS. 18A and 18B).

Figure 18A:
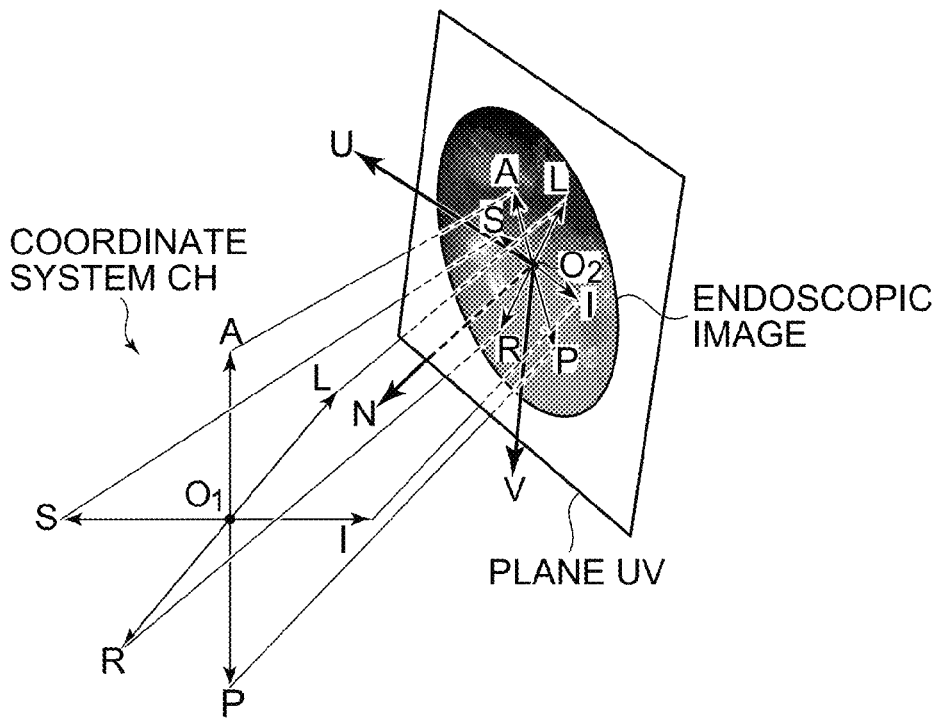
FIGS. 18A and 18B are a diagram showing the manner after the coordinate axes AP, RL and SI are projected onto the endoscopic image.
Figure 18B:
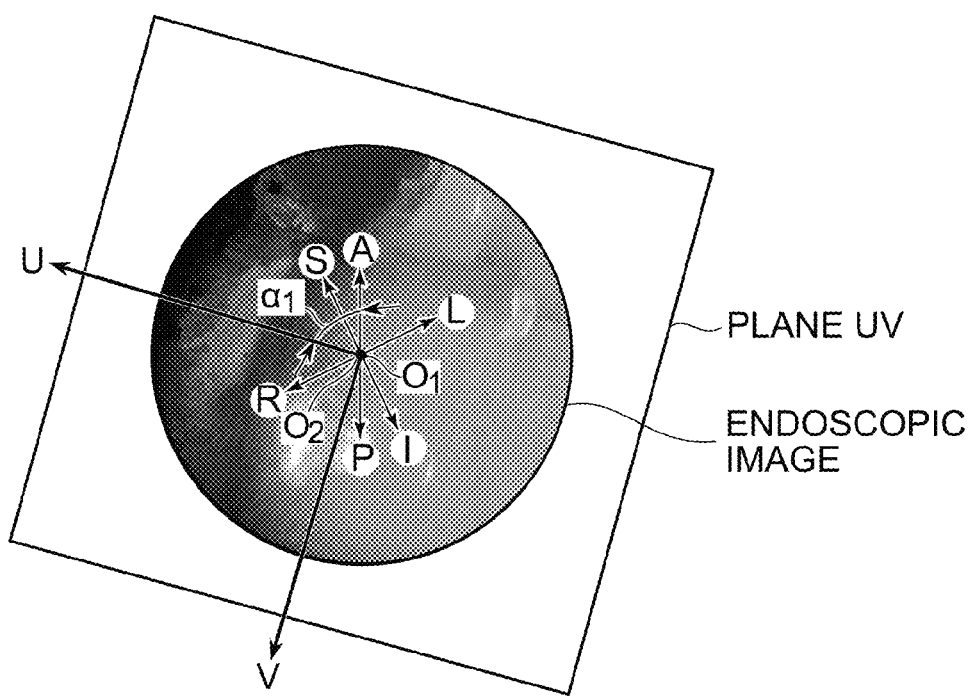

FIGS. 18A and 18B are a diagram showing the manner after the coordinate axes AP, RL and SI are projected onto the endoscopic image. FIG. 18A is a schematic diagram for explaining a way of projecting the coordinate axes AP, RL and SI onto the endoscopic image, and FIG. 18B is a diagram in the case where FIG. 18A is viewed from the direction of the vector N.

By projecting the coordinate axes AP, RL and SI onto the endoscopic image, it is possible to obtain the correspondence between the coordinate axes AP, RL and SI and the portion displayed on the endoscopic image. The projected coordinate axes AP, RL and SI are displayed on the display unit 10 by the display control unit 83 together with the endoscopic image (refer to FIGS. 19A and 19B).

Figure 19A:
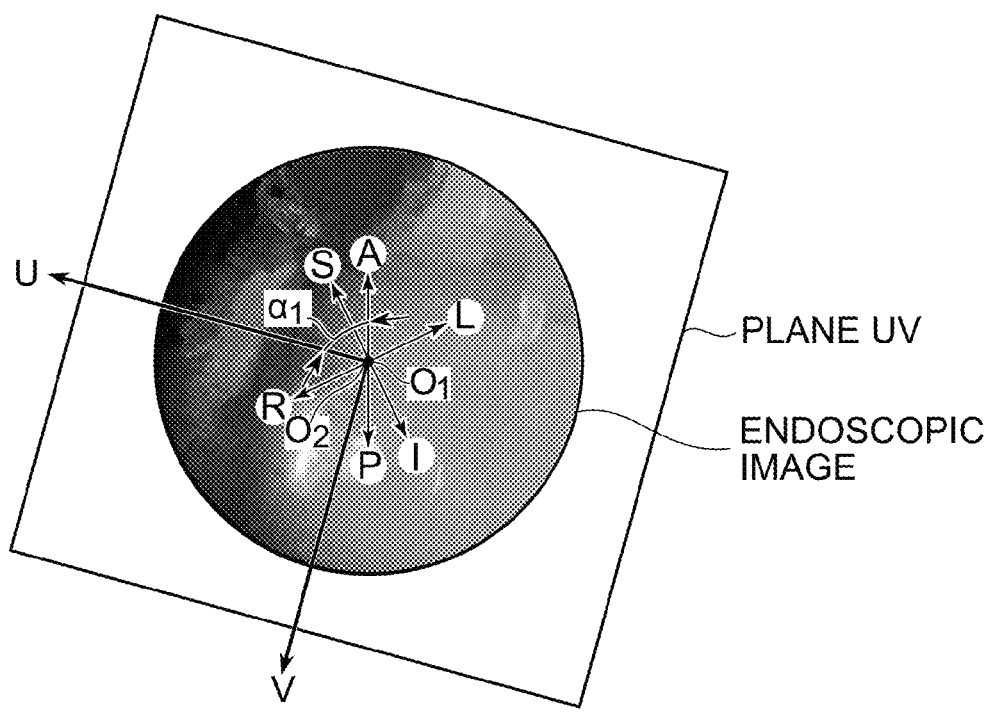
FIGS. 19A and 19B are a diagram for explaining a way of displaying the coordinate axes AP, RL and SI and the endoscopic image on the display unit.
Figure 19B:
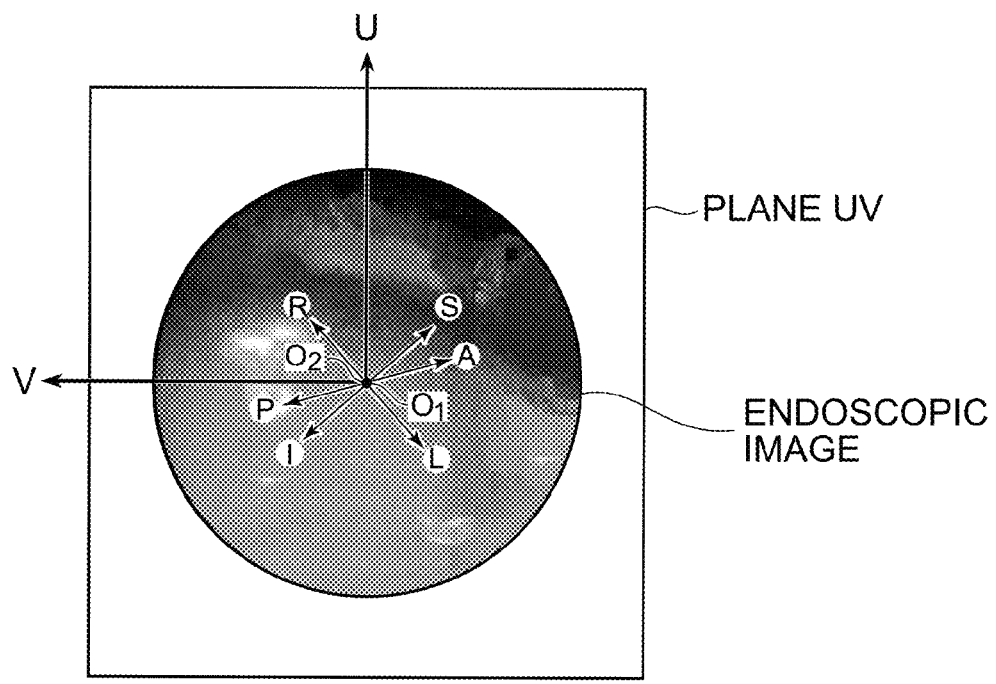

FIGS. 19A and 19B are a diagram for explaining a way of displaying the coordinate axes AP, RL and SI and the endoscopic image on the display unit 10.

Figure 20A:
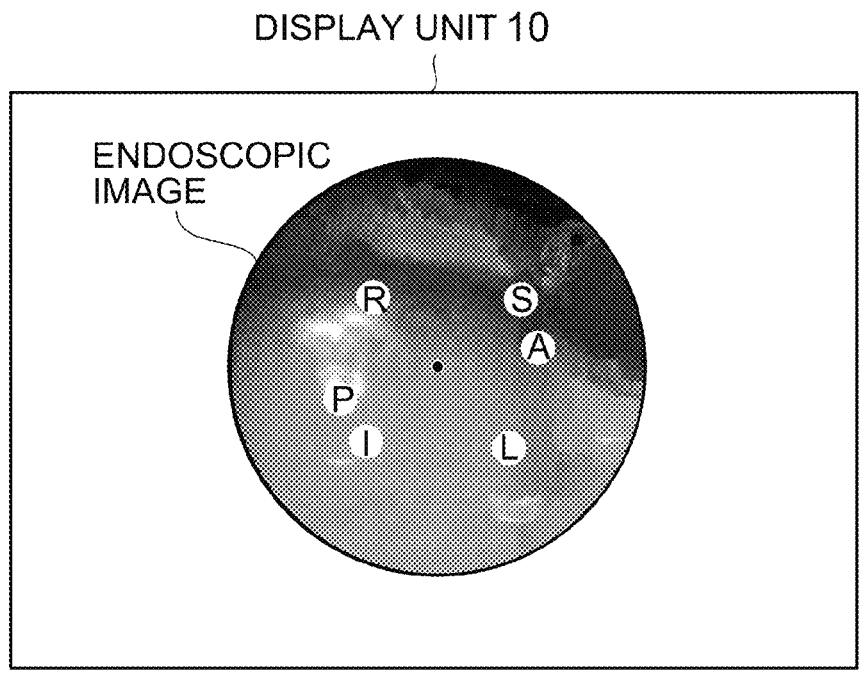
FIGS. 20A and 20B are a diagram schematically showing one example of the endoscopic image displayed on the display unit.
Figure 20B:
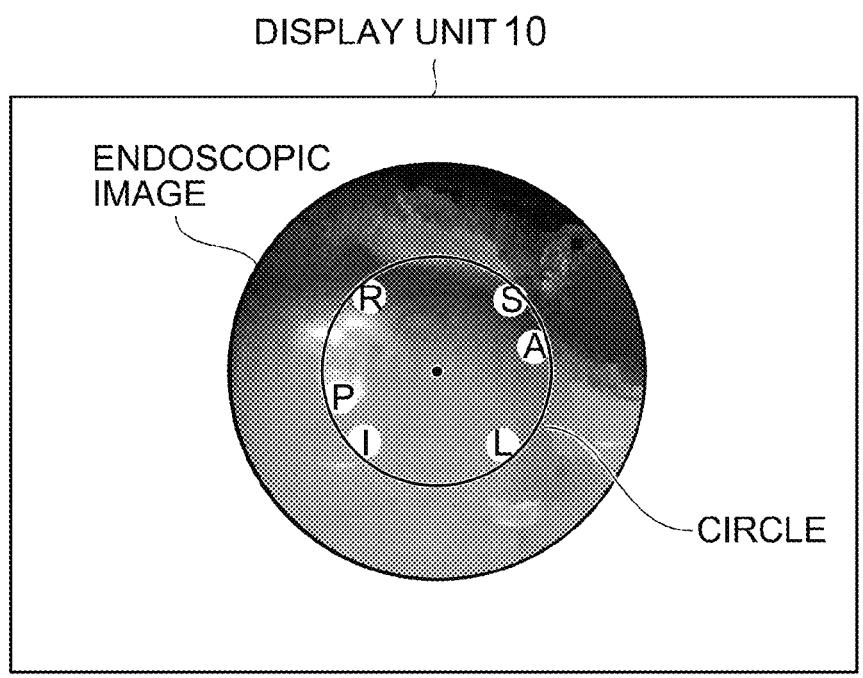

Since the endoscopic image is being rotated by $\alpha=\alpha 1$ (refer to FIG. 19A), the endoscopic image is rotated clockwise by $\alpha 0$ about the origin O2 of the vector to restore the rotational angle of the endoscopic image (refer to FIG. 19B). Consequently, it is possible to turn the vector U to the upper side and turn the vector V to the left side. After the endoscopic image has been rotated in this way, the endoscopic image is displayed on the display unit 10. One example of the endoscopic image displayed on the display unit 10 is schematically illustrated in FIGS. 20A and 20B. FIG. 20A shows an example in which a circle is not displayed, and FIG. 20B shows example in which the circle is displayed. Since the coordinate axes AP, RL and SI have been projected onto the endoscopic image, the operator is able to visually and easily recognize by simply looking at the endoscopic image, that the lower side of the endoscopic image is an L-axis side (left half body side) and the upper side of the endoscopic image is an R-axis side (right half body side).

Incidentally, in the above description, the three coordinate axes AP, RL and SI have all been displayed on the endoscopic image. It is however unnecessary to display the three coordinate axes AP, RL and SI all. For example, only the two coordinate axes may be displayed. A description will hereinafter be made about the case where only the two coordinate axes are displayed.

Figure 21:
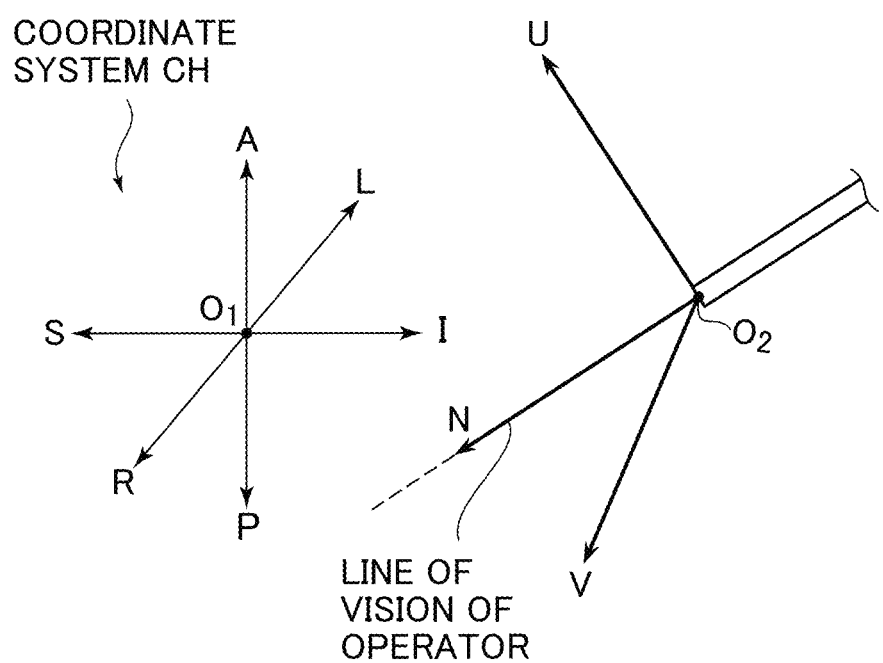
FIG. 21 is a diagram for explaining a way of displaying only the two coordinate axes.

FIG. 21 is a diagram for explaining a way of displaying only the two coordinate axes.

When the operator looks at the endoscopic image, the line of vision of the operator becomes the same direction as the vector N. Therefore, it is considered that knowing the direction of the coordinate axis forming large angle with respect to the vector N, rather than knowing the direction of the coordinate axis forming small angle with respect to the vector N is information useful for the operator to visually recognize the position of the distal end of the endoscope 30. Thus, the coordinate axis forming the largest angle with respect to the vector N, and the coordinate axis forming the second largest angle with respect to the vector N are selected from among the three coordinate axes, and only the selected coordinate axes may be displayed (refer to FIG. 22).

Figure 22:
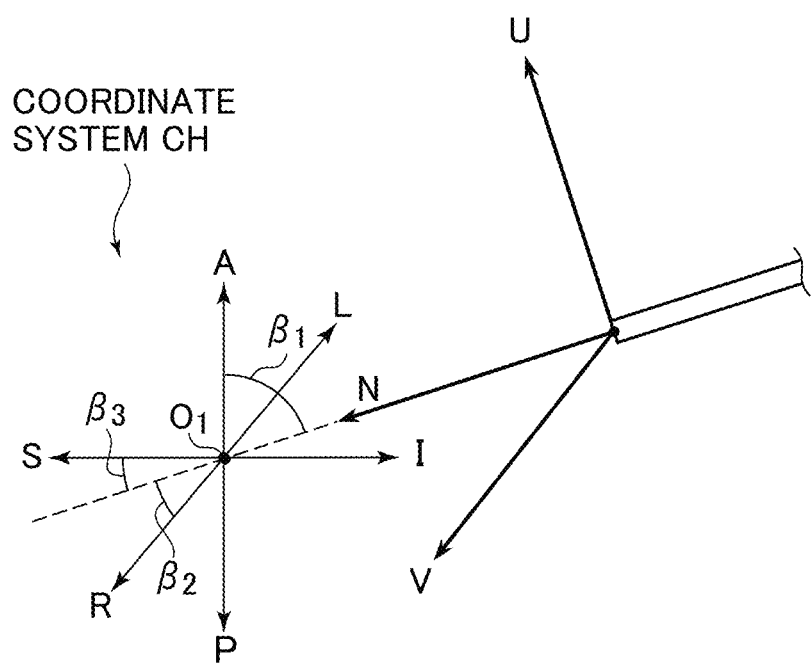
FIG. 22 is a diagram for explaining a way of selecting each of the coordinate axes forming large angle with respect to the vector N from among the three coordinate axes.

FIG. 22 is a diagram for explaining a way of selecting each of the coordinate axes forming large angle with respect to the vector N from among the three coordinate axes.

First, the vectors N, U and V of the endoscope 30 are translated in such a manner that the origin $O_1$ of the coordinate system CH is positioned on the extension of the vector N. By translating the vectors N, U and V in this manner, angles $\beta 1$, $\beta 2$ and $\beta 3$ between the vector N and three coordinate axes AP, RL and SI are defined.

Figure 23:
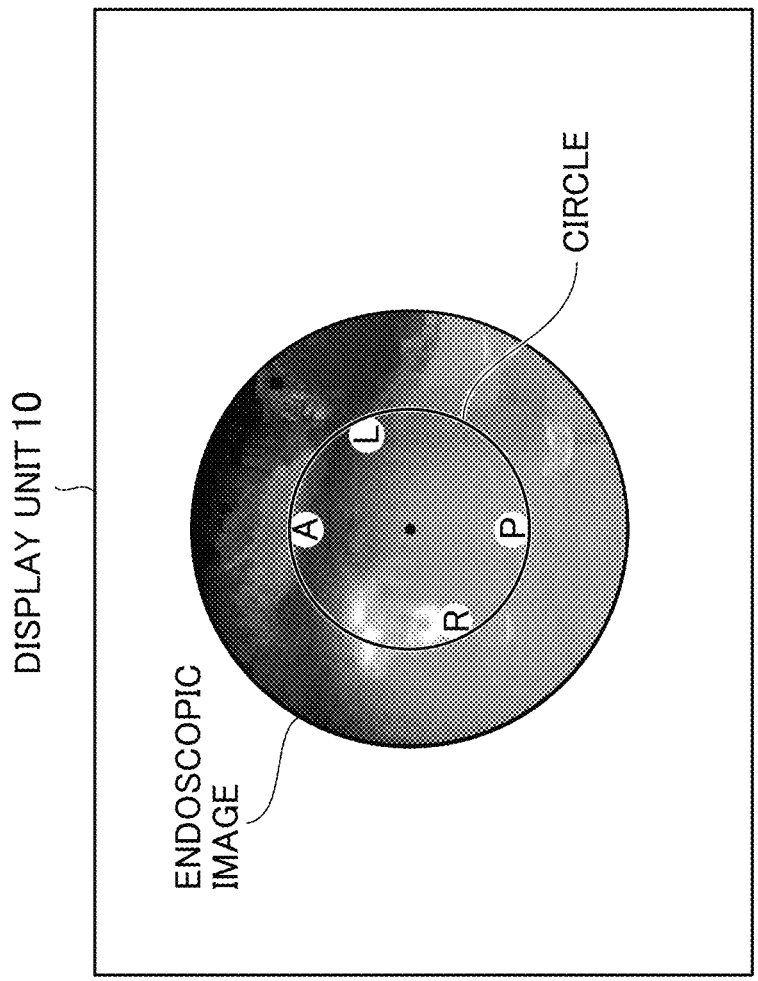
FIG. 23 is a diagram showing an example in which the two coordinate axes AP and RL are displayed on the endoscopic image.

The selecting unit 82 (refer to FIG. 1) calculates the angles $\beta 1$, $\beta 2$ and $\beta 3$. Thus, the coordinate axis forming the largest angle with respect to the vector N, and the coordinate axis forming the second largest angle with respect to the vector N can be selected by comparing the angles $\beta 1$, $\beta 2$ and $\beta 3$. For example, when there is a relationship of $\beta 1 > \beta 2 > \beta 3$ among the angles $\beta 1$, $\beta 2$ and $\beta 3$, the coordinate axis forming maximum angle with respect to the vector N is AP, and the coordinate axis forming the second largest angle with respect to the vector N is RL. Thus, the two coordinate axes AP and RL are displayed. FIG. 23 shows an example in which the two coordinate axes AP and RL are displayed on the endoscopic image. By displaying only the two coordinate axes out of the three coordinate axes on the endoscopic image, only the coordinate axes which are high on the operator's priority order to recognize the position of the distal end of the endoscope 30 can be displayed.

(2) Second Embodiment

Figure 24:
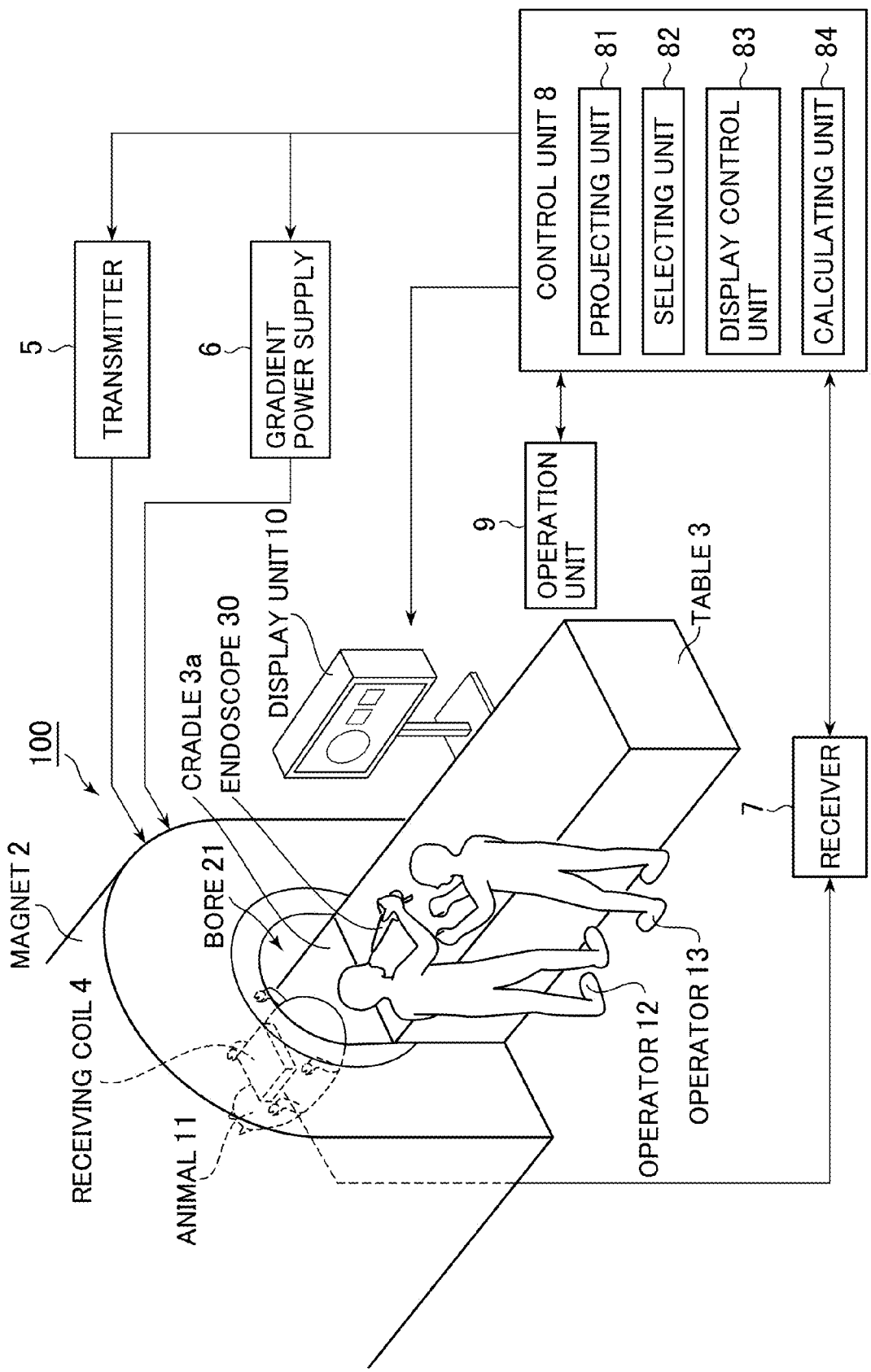
FIG. 24 is a schematic diagram of an MR apparatus of a second embodiment.

FIG. 24 is a schematic diagram of an MR apparatus 200 of a second embodiment.

The MR apparatus 200 has a calculating unit 84 which calculates an elevation angle $\theta$ of the endoscope 30. Incidentally, other configurations are the same as those in the first embodiment. The elevation angle $\theta$ will be described below.

Figure 25:
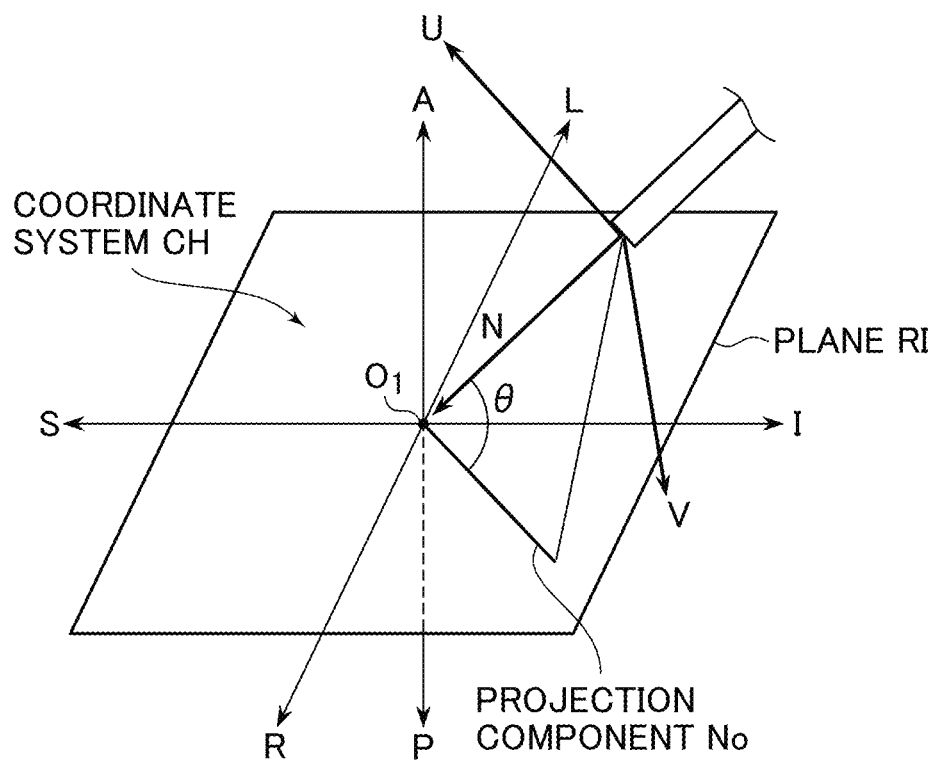
FIG. 25 is an explanatory diagram of an elevation angle θ.

FIG. 25 is an explanatory diagram of the elevation angle $\theta$.

Figure 26:
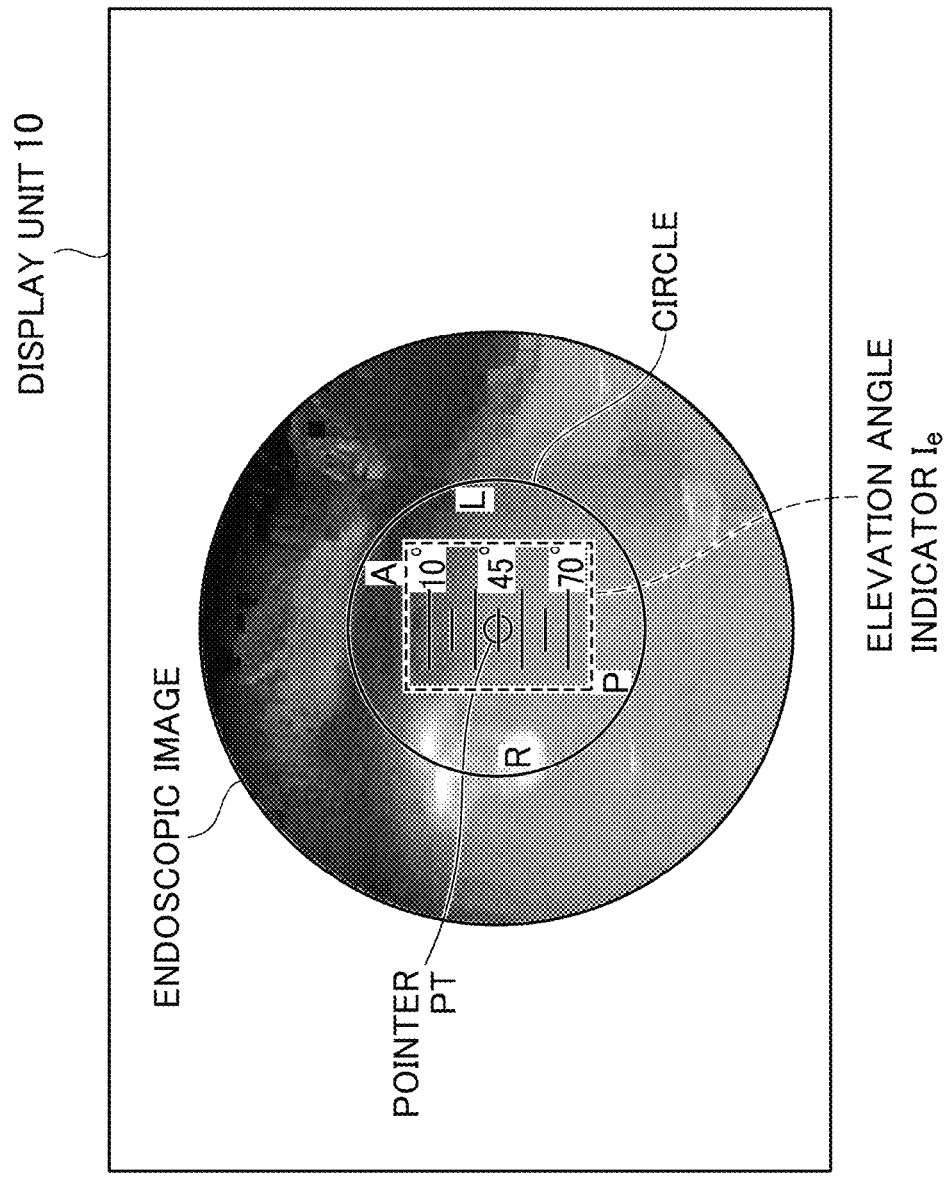
FIG. 26 is a diagram showing one example of a display method of the elevation angle θ displayed on the display unit.

Even when the elevation angle $\theta$ is determined, as with the first embodiment, the vectors N, U and V of the endoscope 30 are translated in such a manner that the vector N of the endoscope 30 crosses the origin O1 of the coordinates. A plane RI defined by the SI axis and the RL axis is shown in FIG. 25. The elevation angle $\theta$ is defined as the angle formed between a projection component N0 to the plane RI of the vector N and the vector N. The elevation angle $\theta$ is displayed on the display unit 10 by the display control unit 83. FIG. 26 shows one example of a display method of the elevation angle $\theta$ displayed on the display unit 10. In FIG. 26, an elevation angle indicator Ie for indicating the elevation angle $\theta$ is displayed in the central portion of the endoscopic image. The elevation angle indicator Ie has a pointer PT indicating the value of the elevation angle $\theta$. There is shown in FIG. 26, an example in which the elevation angle indicator Ie indicates an angular range of 10° to 70°, and the pointer indicates $\theta=45°$. Thus, since the operator is able to confirm the elevation angle $\theta$ ($\theta=45°$) simultaneously while looking the endoscopic image displayed on the display unit 10, the operator is capable of recognizing how the distal end of the endoscope 30 is inclined relative to the plane RI.

A description will next be made about how the display of the elevation angle $\theta$ changes when the value of the elevation angle $\theta$ is changed.

Figure 27:
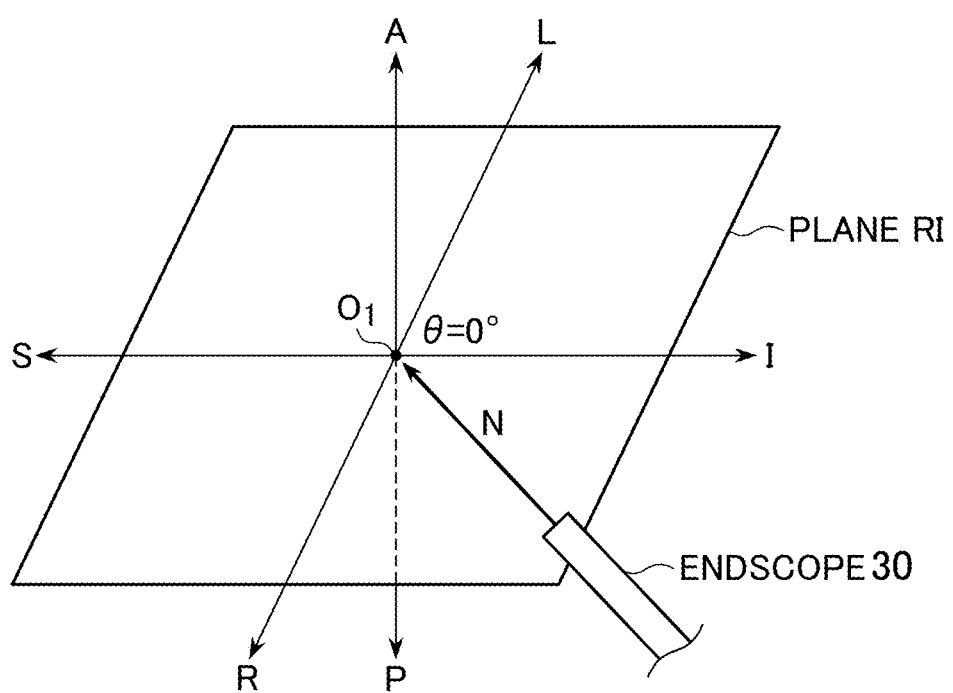
FIG. 27 is a diagram showing a positional relationship between the coordinate system CH and the vector N in the case where the elevation angle θ of the distal end of the endoscope is θ=0°.
Figure 28:
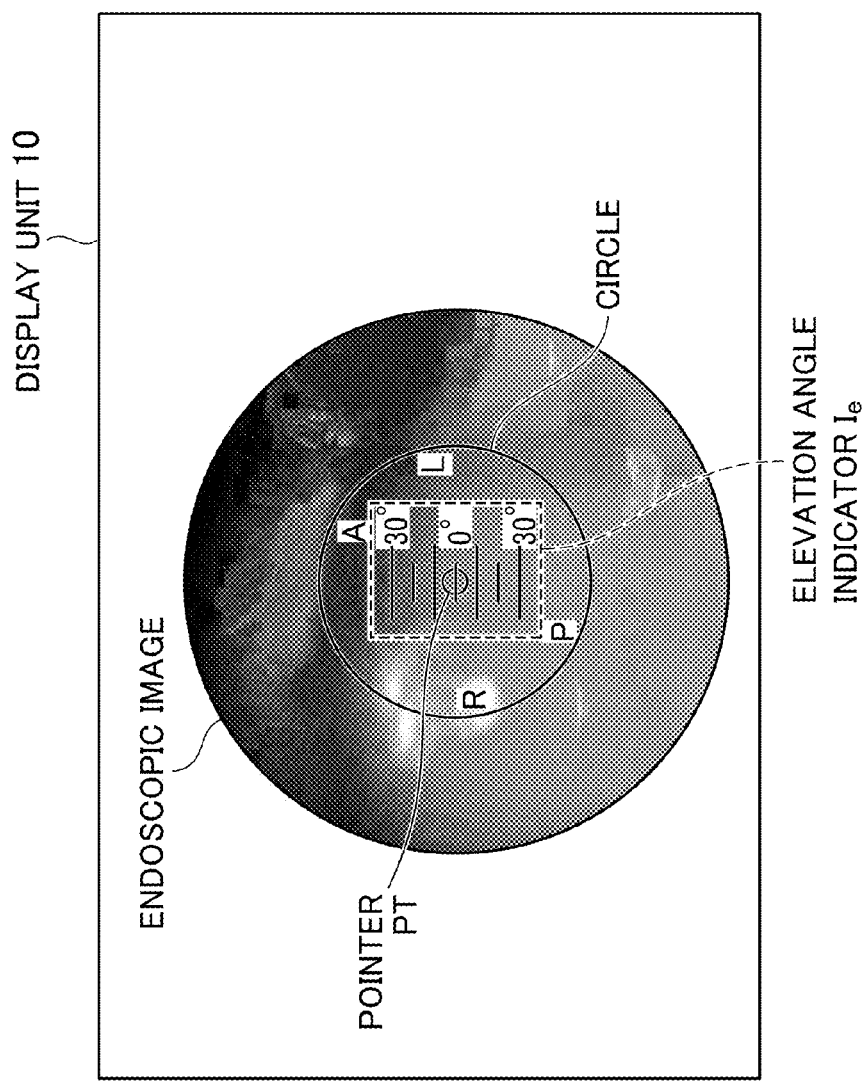
FIG. 28 is a diagram showing one example of an elevation angle indicator Ie when θ=0°.

FIG. 27 is a diagram showing a positional relationship between the coordinate system CH and the vector N in the case where the elevation angle $\theta$ of the distal end of the endoscope 30 is $\theta=0°$, and FIG. 28 is a diagram showing one example of the elevation angle indicator Ie when $\theta=0°$.

In the case of $\theta=0°$, the vector N becomes parallel to the plane RI. The elevation angle indicator Ie indicates an angular range of −30° to 30°, and the pointer indicates $\theta=0°$. Thus, since the operator is able to confirm the elevation angle $\theta$ ($\theta=0°$) simultaneously while looking at the endoscopic image displayed on the display unit 10, the operator is capable of recognizing that the vector N of the endoscope 30 is parallel to the plane RI.

A description will next be made about the elevation angle indicator in the case where the elevation angle $\theta$ of the distal end of the endoscope 30 is $\theta=-45°$.

Figure 29:
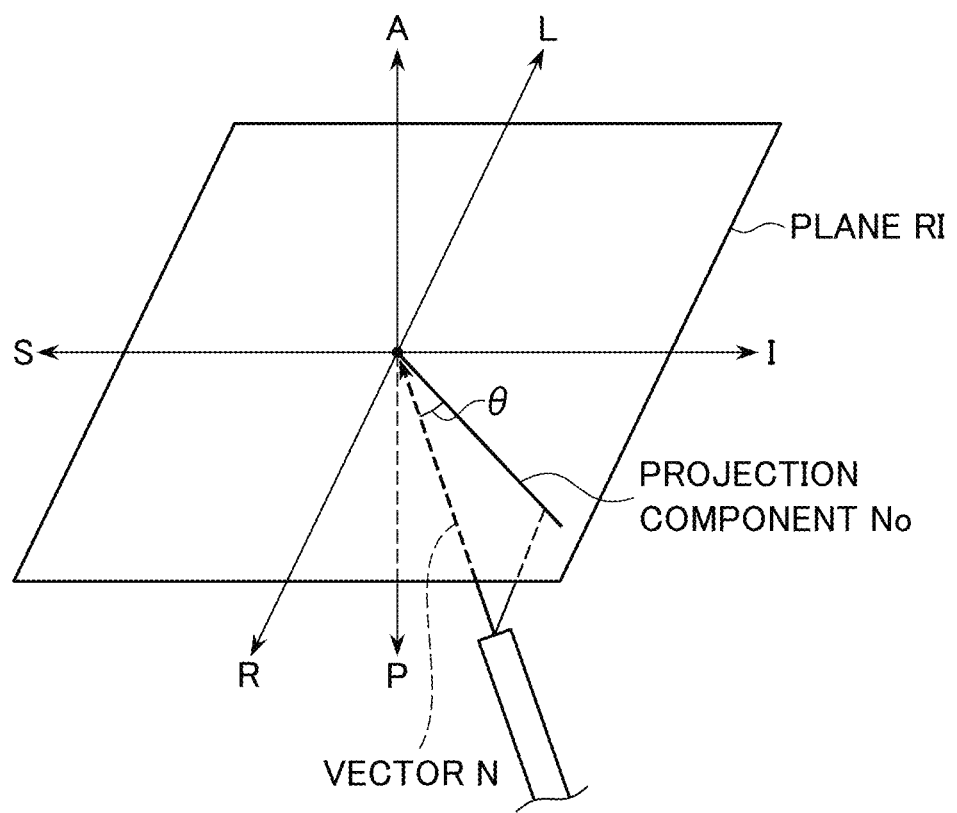
FIG. 29 is a diagram showing a positional relationship between the coordinate system CH and the vector N in the case where the elevation angle θ of the distal end of the endoscope is θ=−45°.
Figure 30:
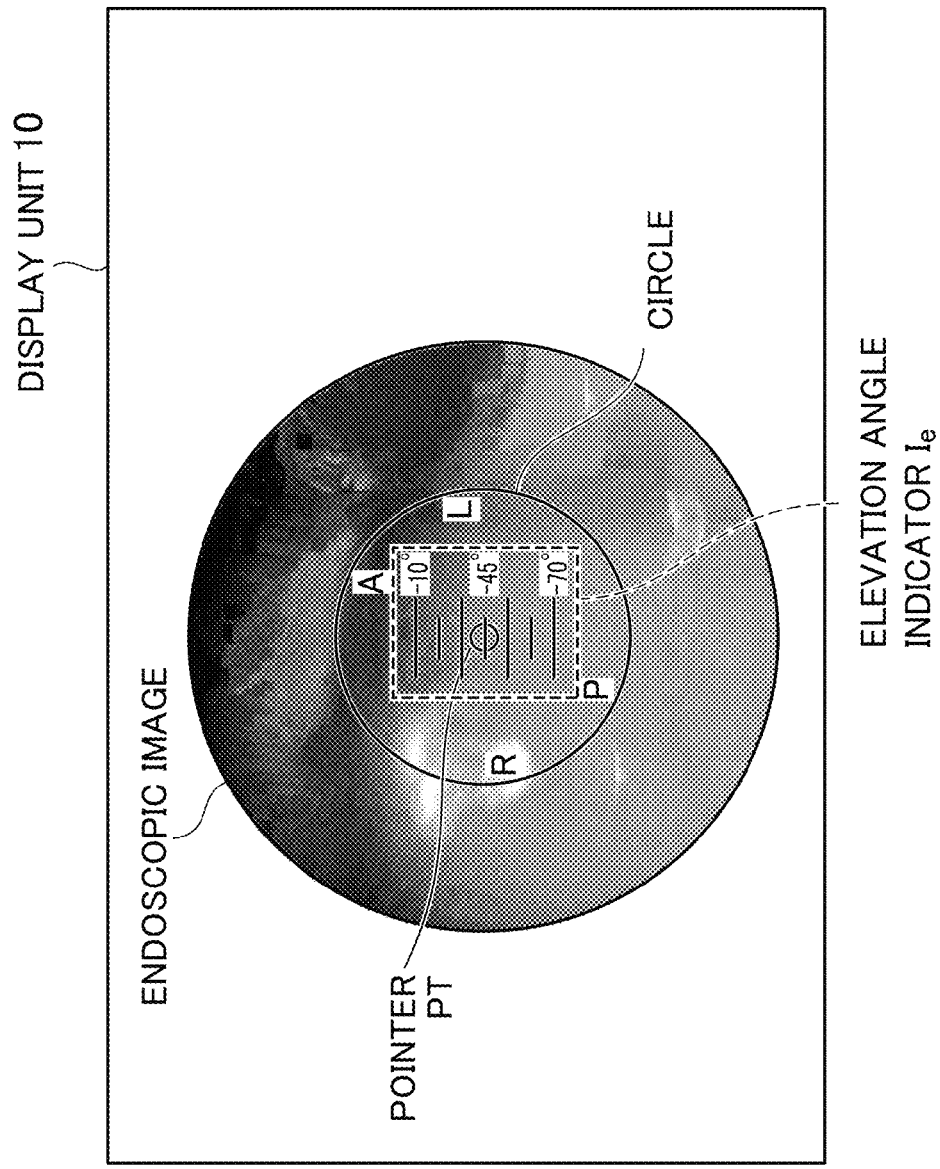
FIG. 30 is a diagram showing one example of the elevation angle indicator Ie when θ=−45°.

FIG. 29 is a diagram showing a positional relationship between the coordinate system CH and the vector N in the case where the elevation angle $\theta$ of the distal end of the endoscope 30 is $\theta=-45°$, and FIG. 30 is a diagram showing one example of the elevation angle indicator Ie when $\theta=-45°$.

In the case of $\theta=-45°$, the vector N is oriented obliquely upward to the plane RI. The elevation angle indicator indicates an angular range of −10° to −70°, and the pointer indicates $\theta=-45°$. Thus, since the operator is able to confirm the value of the elevation angle $\theta$ ($\theta=-45°$) simultaneously while looking at the endoscopic image displayed on the display unit 10, the operator is capable of recognizing that the distal end of the endoscope 30 is oriented obliquely upward.

(3) Third Embodiment

A third embodiment will be described below. In the third embodiment, the calculating unit 84 is configured to calculate an azimuthal angle $\phi$ in addition to the elevation angle $\theta$, but other configurations are the same as those in the second embodiment. The azimuthal angle $\phi$ will be described below.

Figure 31:
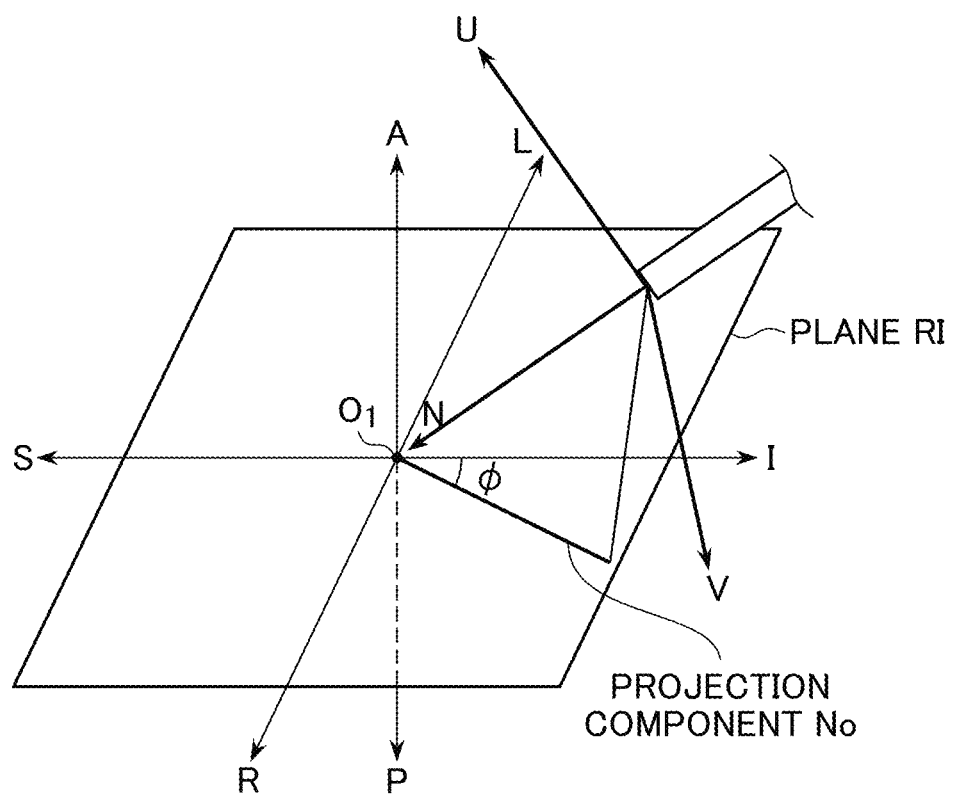
FIG. 31 is an explanatory diagram of an azimuthal angle φ.

FIG. 31 is an explanatory diagram of the azimuthal angle $\phi$.

Figure 32:
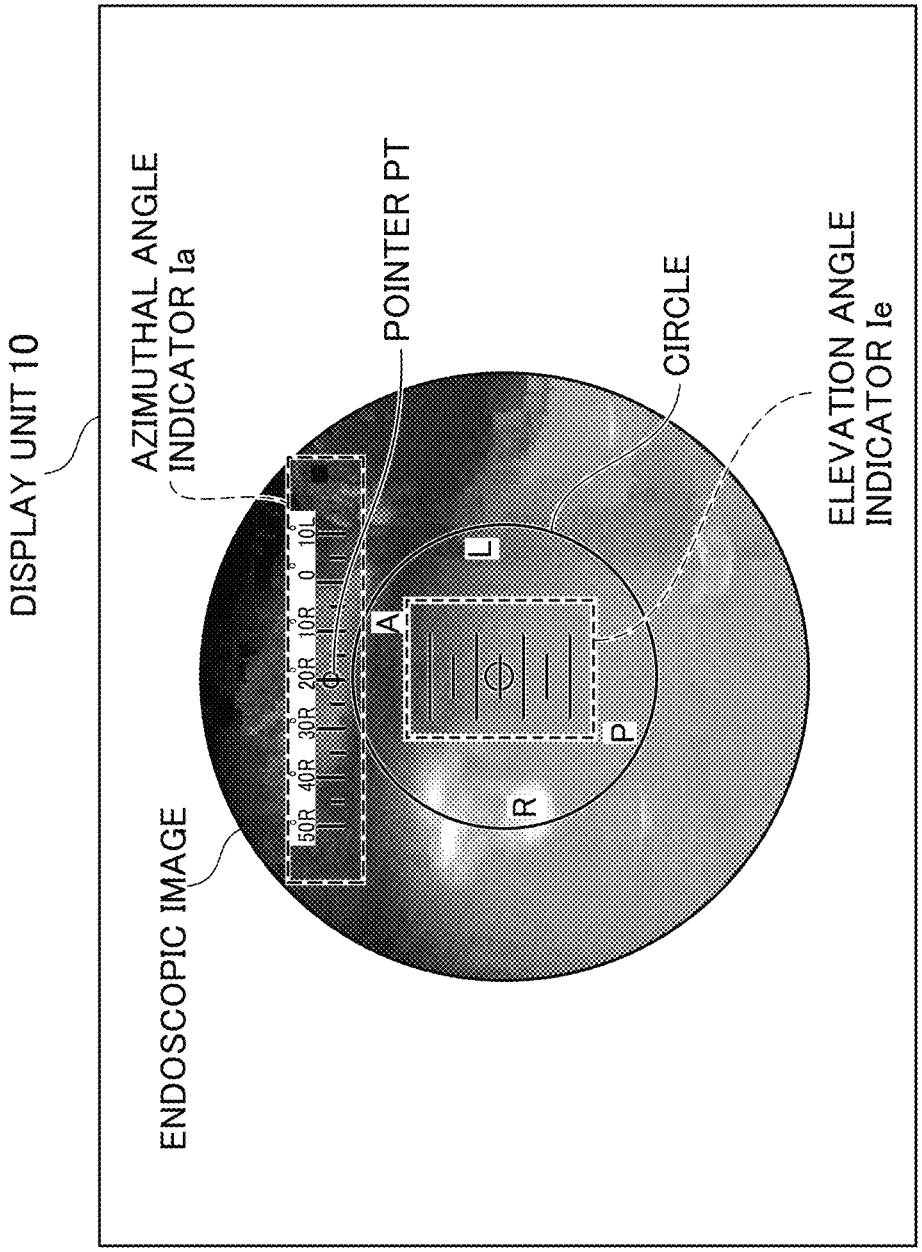
FIG. 32 is a diagram showing one example of a display method of the azimuthal angle φ displayed on the display unit.

Even when the azimuthal angle $\phi$ is determined, the vectors N, U and V of the endoscope 30 are translated such that the vector N of the endoscope 30 crosses the origin $O_1$ of the coordinates. The azimuthal angle $\phi$ is defined as an angle between the projection NO to the plane RI of the vector N and the SI axis. This angle $\phi$ is displayed on the display unit 10 by the display control unit 83. FIG. 32 shows one example of a display method of the azimuthal angle $\phi$ displayed on the display unit 10. In FIG. 32, an azimuthal angle indicator Ia for indicating the azimuthal angle $\phi$ is displayed in the upper part of the circle in the endoscopic image. The azimuthal angle indicator Ia has a pointer PT indicating the value of the azimuthal angle $\phi$. There is shown in FIG. 32, an example in which the azimuthal angle indicator Ia indicates an angular range of 50° R to 10° L, and the pointer PT indicates $\phi=20°$ R. Incidentally, the angle representing $\phi$ is provided with the alphabet "R" or "L" together. The alphabet "R" indicates that the angle $\phi$ is on the R-axis side relative to the SI axis, and the alphabet "L" indicates that the angle $\phi$ is on the L-axis side relative to the SI axis. Accordingly, $\phi=20°$ R indicated by the pointer PT represents a 20° inclination to the R-axis side relative to the SI axis. Since the operator is able to confirm the azimuthal angle φ (θ=20° R) simultaneously while looking at the endoscopic image displayed on the display unit 10, the operator is capable of recognizing how the distal end of the endoscope 30 is inclined with respect to the SI axis.

A description will next be made about how the display of the azimuthal angle φ changes when the value of the azimuthal angle φ is changed.

Figure 33:
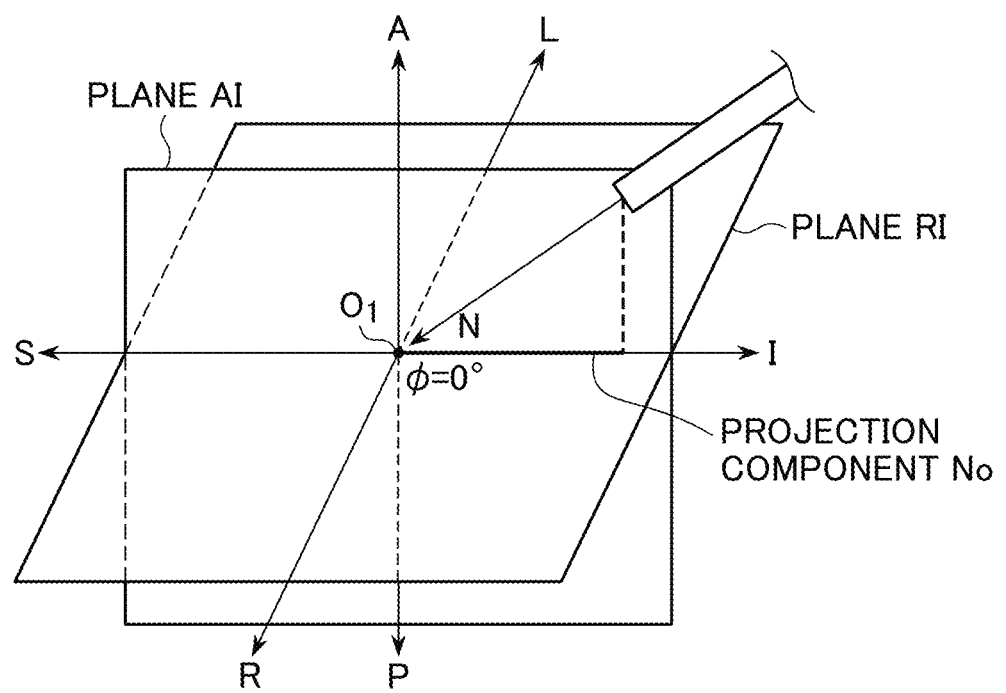
FIG. 33 is a diagram showing a positional relationship between the coordinate system CH and the vector N in the case where the azimuthal angle φ of the distal end of the endoscope is φ=0°.
Figure 34:
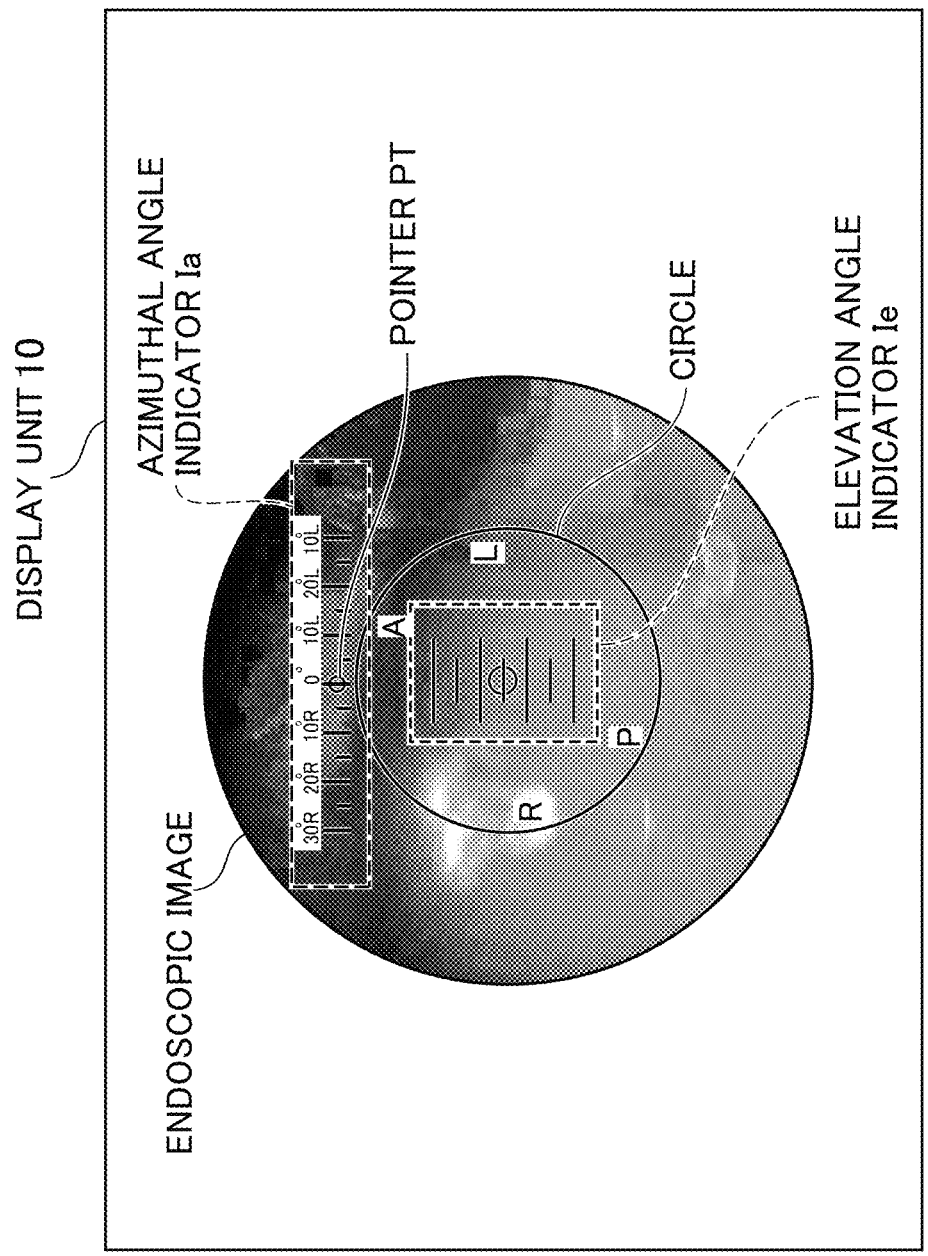
FIG. 34 is a diagram showing one example of an azimuthal angle indicator Ia when φ=0°.

FIG. 33 is a diagram showing a positional relationship between the coordinate system CH and the vector N in the case where the azimuthal angle φ of the distal end of the endoscope 30 is θ=0°, and FIG. 34 is a diagram showing one example of the azimuthal angle indicator Ia when φ=0°.

In addition to the plane RI, the plane AI is displayed in FIG. 33. The plane AI is a plane defined by the SI axis and the AP axis. In the case of φ=0°, the vector N becomes parallel to the plane AI. The azimuthal angle indicator indicates an angular range of 30° R to 30° L, and the pointer PT indicates φ=0°. Thus, since the operator is able to confirm the azimuthal angle φ (φ=0°) simultaneously while looking at the endoscopic image displayed on the display unit 10, the operator is capable of recognizing that the vector N of the endoscope 30 is parallel to the plane AI.

A description will next be made about the azimuthal angle indicator in the case where the azimuthal angle φ of the distal end of the endoscope 30 is φ=20° L.

Figure 35:
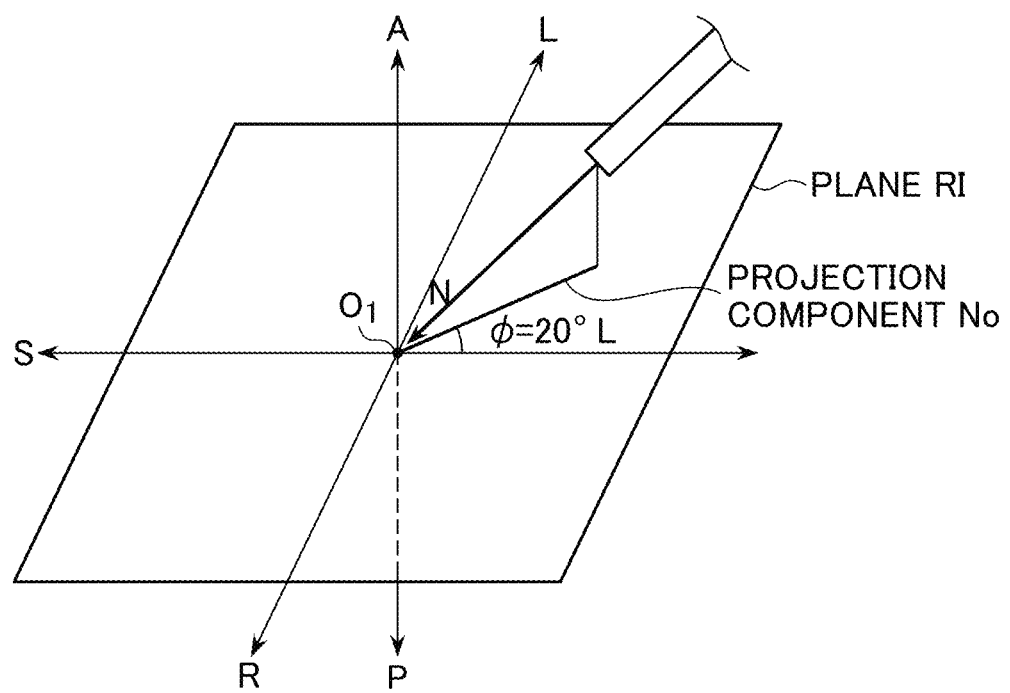
FIG. 35 is a diagram showing a positional relationship between the coordinate system CH and the vector N in the case where the azimuthal angle φ of the distal end of the endoscope is φ=20° L.
Figure 36:
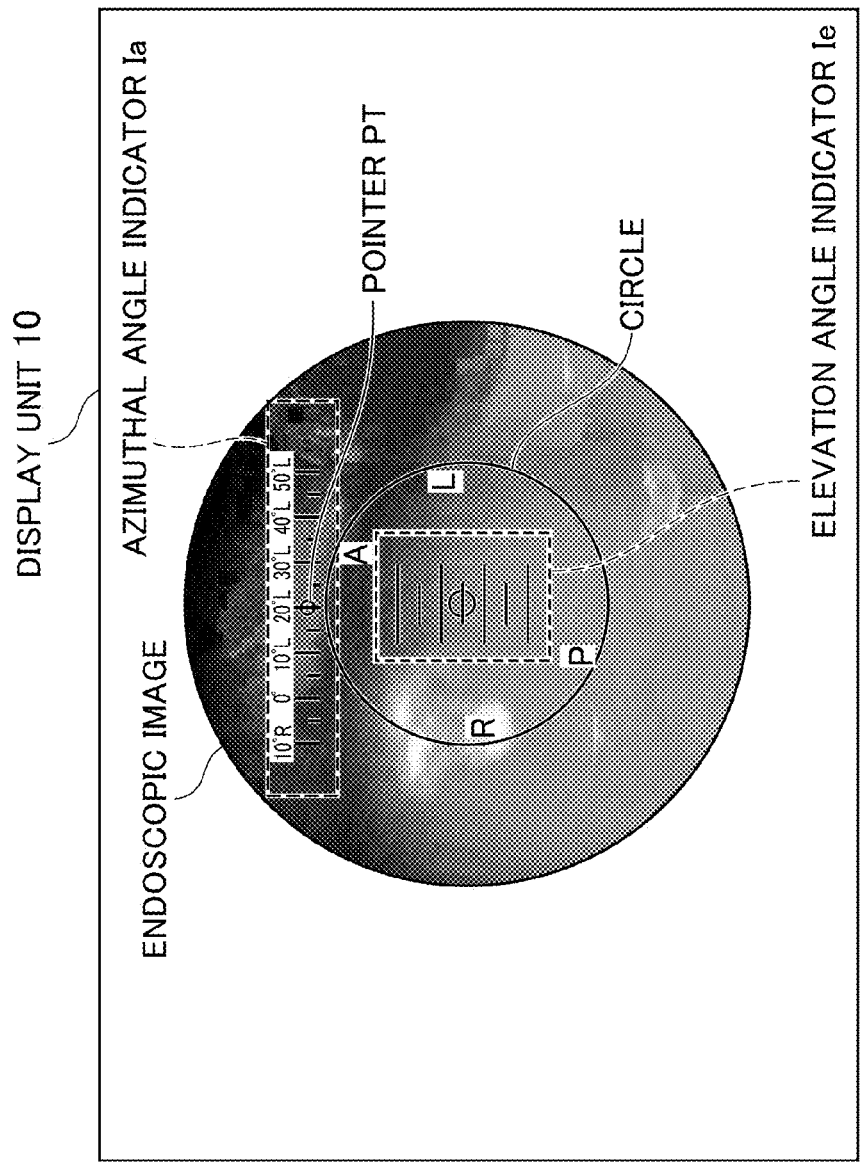
FIG. 36 is a diagram showing one example of the azimuthal angle indicator Ia when φ=20° L.

FIG. 35 is a diagram showing a positional relationship between the coordinate system CH and the vector N in the case where the azimuthal angle φ of the distal end of the endoscope 30 is φ=20° L, and FIG. 36 is a diagram showing one example of the azimuthal angle indicator Ia when φ=20° L.

The azimuthal angle indicator indicates an angular range of 10° R to 50° L, and the pointer indicates φ=20° L. Thus, since the operator is able to confirm the azimuthal angle φ (φ=20° L) simultaneously while looking at the endoscopic image displayed on the display unit 10, the operator can understand that the vector N is tilted 20° with respect to the SI axis.

(4) Fourth Embodiment

A fourth embodiment will be described below. Incidentally, the fourth embodiment is the same as the second embodiment in terms of the hardware configuration of the MR apparatus.

Figure 37:
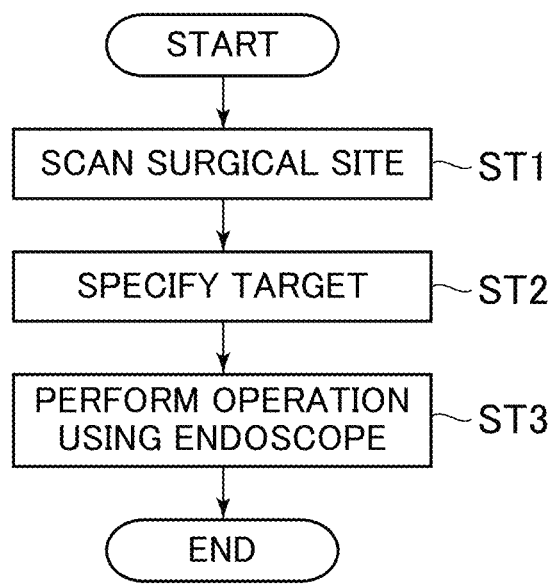
FIG. 37 is a diagram showing a flow for performing surgery in the fourth embodiment.

FIG. 37 is a diagram showing a flow for performing surgery in the fourth embodiment.

Figure 38:
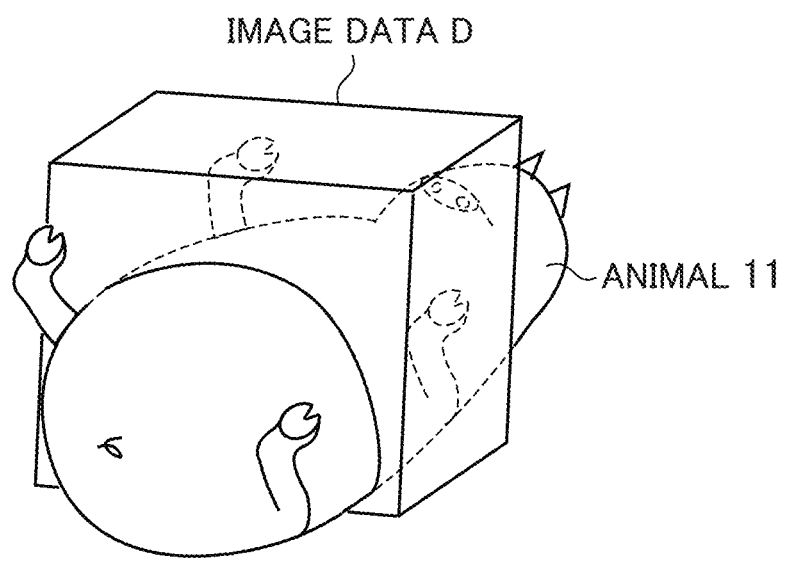
FIG. 38 is a diagram schematically showing image data D obtained by a scan.

In Step ST1, a scan for acquiring image data of a surgical site is performed. FIG. 38 is a diagram schematically showing the image data D obtained by the scan. After the scan has been performed, the flow proceeds to Step ST2.

Figure 39:
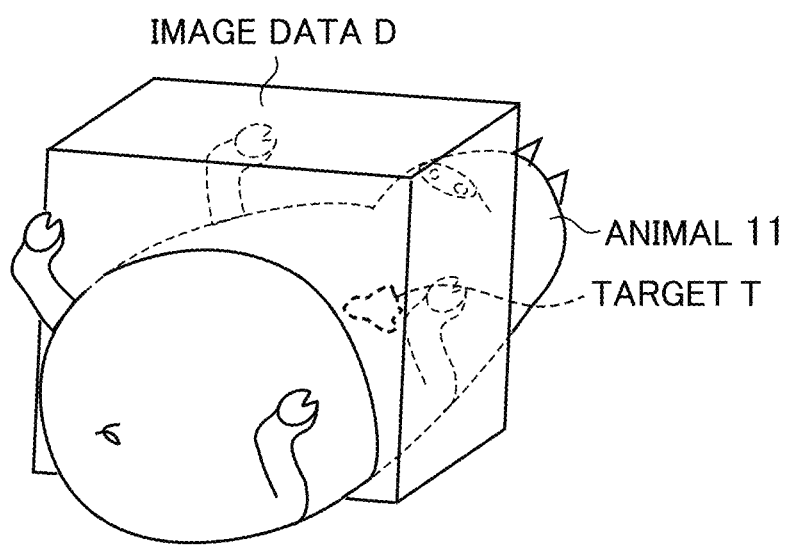
FIG. 39 is a diagram showing a target T specified by an operator.

In Step ST2, the operator specifies a site (hereinafter referred to as a "target") desired to be subject to a surgical procedure by the surgical instrument 34 while looking at the image data D. FIG. 39 shows the target T specified by the operator. After the target T has been specified, the flow proceeds to Step ST3.

In Step ST3, the endoscope 30 is inserted into the animal 11 to perform surgery.

Figure 40A:
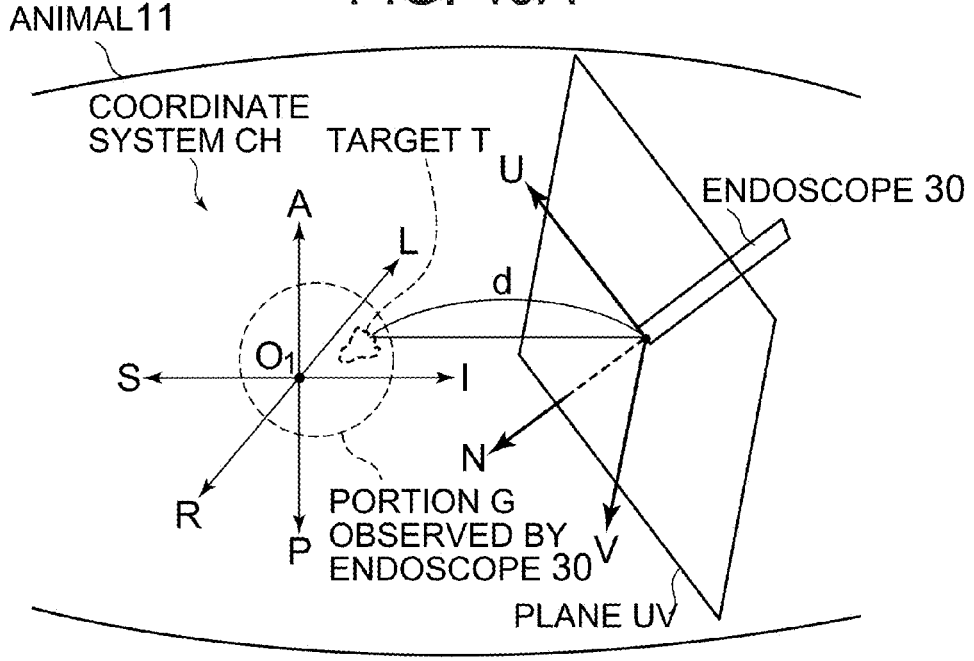
FIGS. 40A and 40B are a diagram schematically showing the manner when the endoscope is inserted into the animal.
Figure 40B:
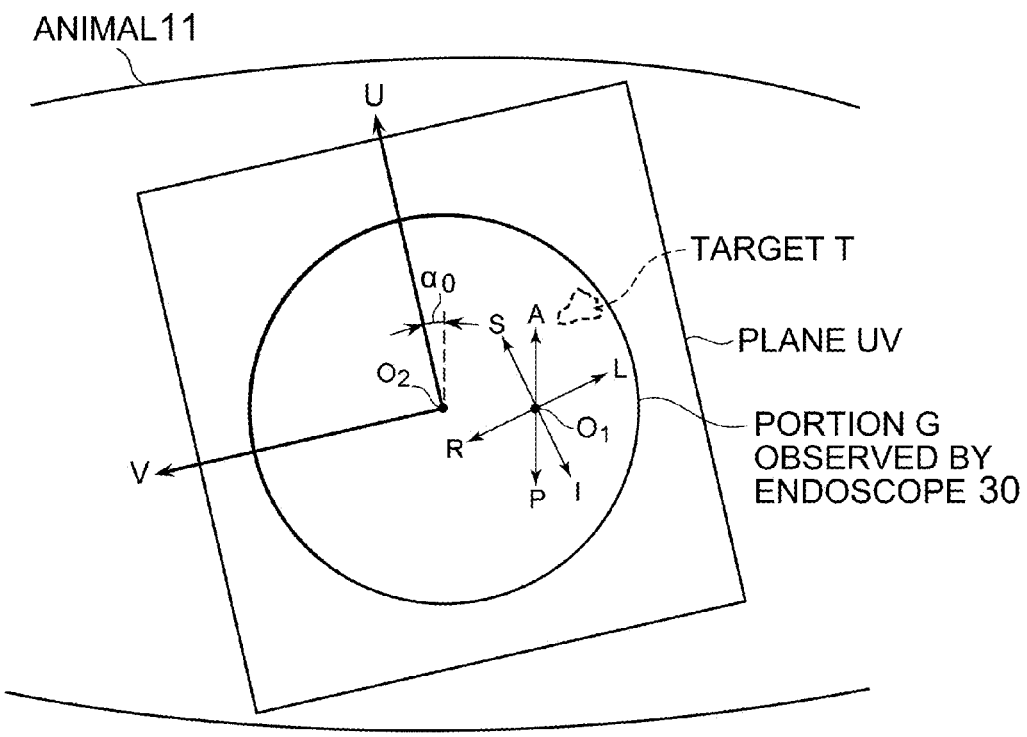

FIGS. 40A and 40B are a diagram schematically showing a situation in which the endoscope 30 is inserted into the animal 11.

FIG. 40A is a diagram showing a positional relationship between the coordinate system CH set to the animal 11 and the vectors N, U and V of the endoscope 30, and FIG. 40B is a diagram in the case where FIG. 40A is viewed from the direction of the vector N.

Figure 41:
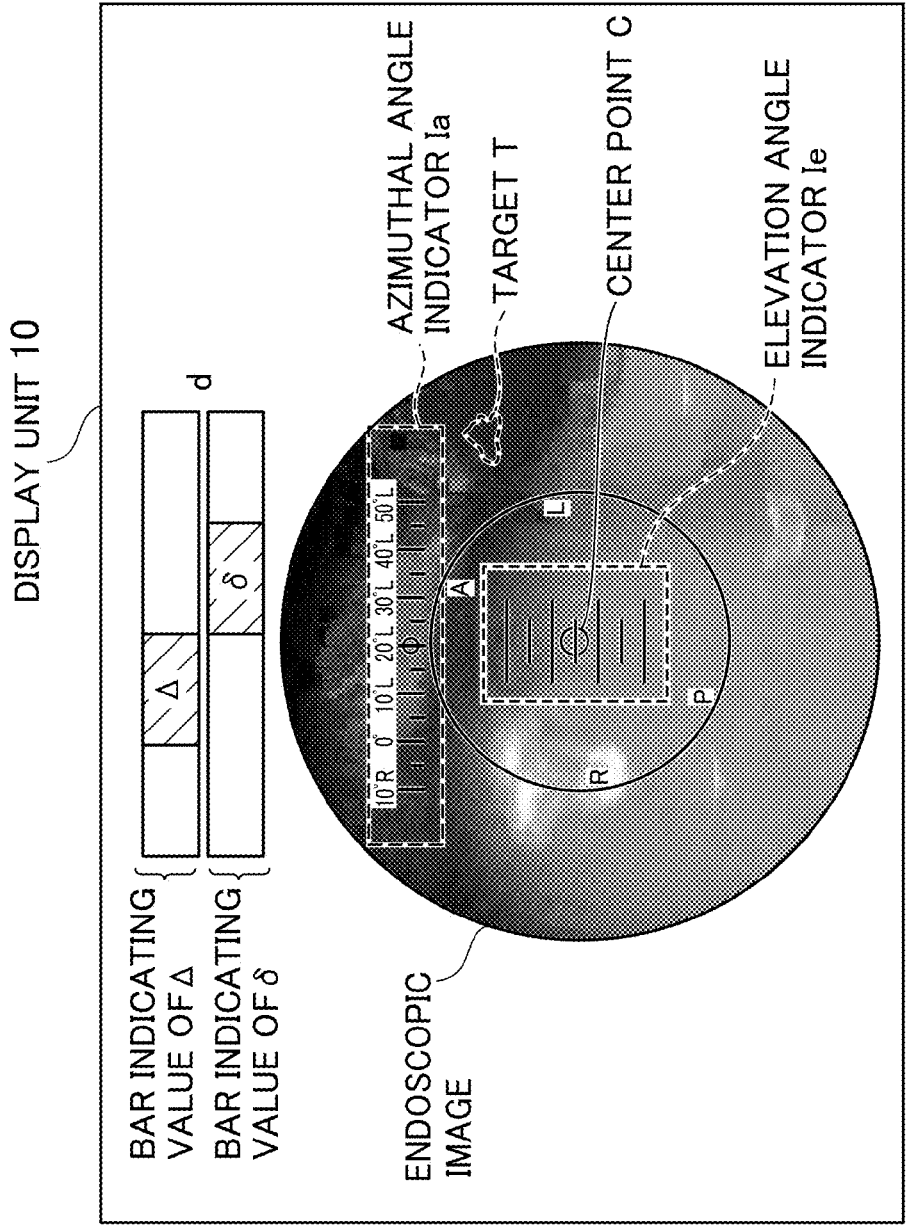
FIG. 41 is a diagram showing one example of the endoscopic image and various information displayed on the display unit.

The operator is able to observe the portion G in the animal 11 by inserting the endoscope 30. At this time, an endoscopic image and various information are displayed on the display unit 10 by the display control unit 83. FIG. 41 shows one example of the endoscopic image and various information displayed on the display unit 10. Specifically, the following (1) to (6) and the like are displayed on the display unit 10:
(1) endoscopic image
(2) coordinate axes
(3) elevation angle indicator Ie
(4) azimuthal angle indicator Ia
(5) target T, and
(6) distances d, δ and Δ.

Incidentally, since (1) to (4) have been described in the first to third embodiments, the description of (1) to (3) is omitted, and (5) and (6) will be described below.

(5) Target T

Figure 42A:
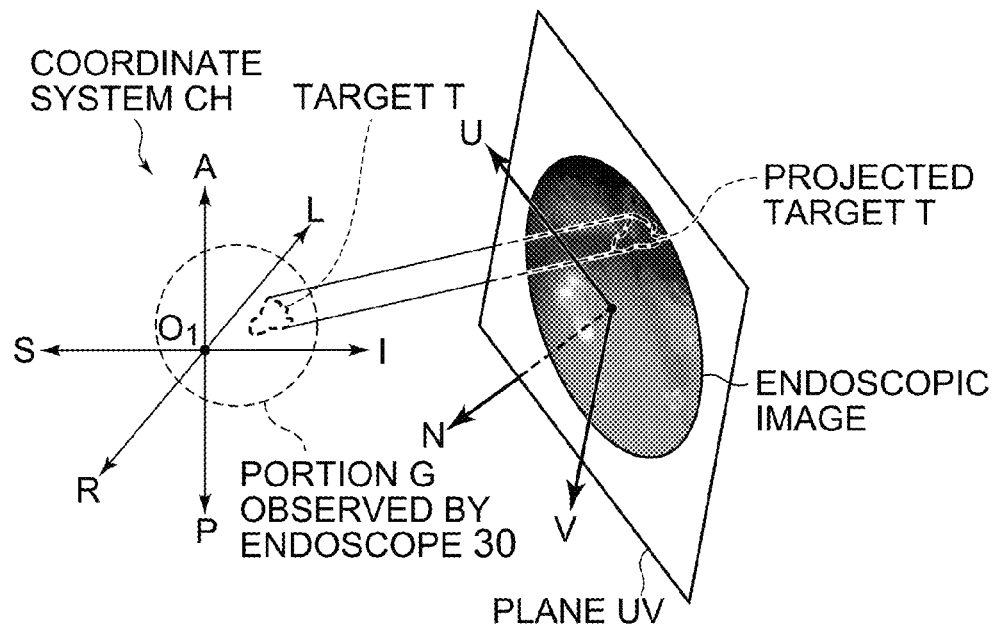
FIGS. 42A and 42B are is a diagram for explaining a way of displaying the target T on the display unit.
Figure 42B:
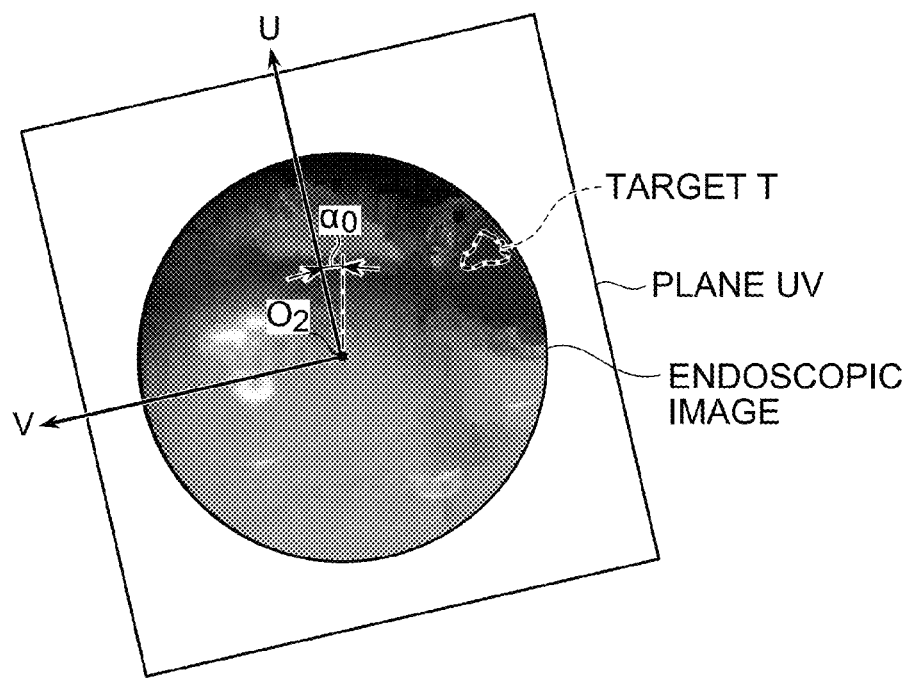

FIGS. 42A and 42B are a diagram for explaining a way of displaying the target T on the display unit 10.

FIG. 42A is a diagram for explaining a way of projecting the target T onto the endoscopic image, and FIG. 42B is a diagram in the case where FIG. 42A is viewed from the direction of the vector N.

The projecting unit 81 projects the target T onto the endoscopic image. It is thus possible to determine a positional relationship between the endoscopic image and the target T. Accordingly, the target T can be displayed within the endoscopic image as shown in FIG. 41.

(6) Distances d, δ and Δ.

Figure 43:
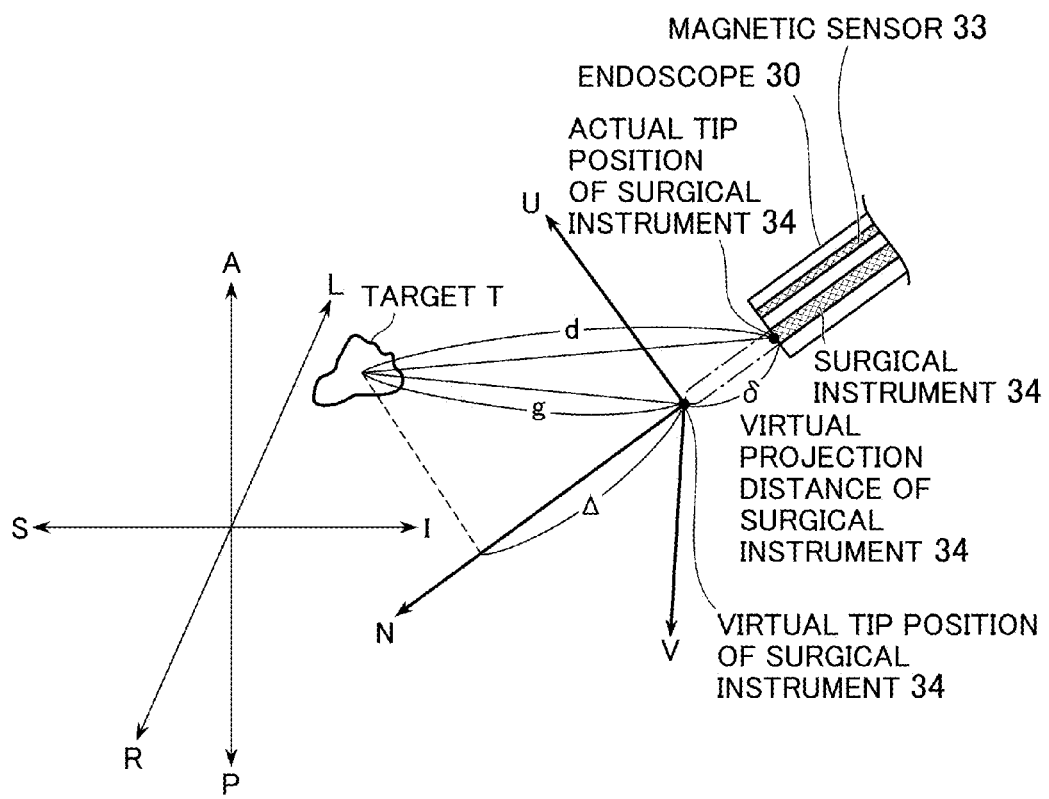
FIG. 43 is an explanatory diagram of distances d, δ and Δ.

FIG. 43 is an explanatory diagram of the distances d, δ and Δ.

The distance d is a distance from the distal end of the endoscope 30 to the target T. The position of the distal end of the endoscope 30 can be detected using the magnetic sensor 33 of the endoscope 30. Further, the position of the target T is determined in Step ST1. Thus, since the position of the distal end of the endoscope 30 and the position of the target T are known, the distance d can be calculated. The distance d is calculated by the calculating unit 84.

The distance δ represents a virtual protrusion distance of the surgical instrument 34 in the case where the surgical instrument 34 is assumed to have been protruded from the endoscope 30. In this case, the vectors U and V are translated in the direction of the vector N by the distance δ. The distance δ is set by the operator.

The distance Δ represents the length of a projection component obtained by projecting a distance g from the virtual tip position of the surgical instrument 34 to the target T onto the vector N. The distance g can be calculated from the virtual tip position of the surgical instrument 34 and the position of the target T. Thus, the distance Δ can be calculated by projecting the distance g onto the vector N. The distance Δ is calculated by the calculating unit 84.

Thus, the target T, the distances d, δ and Δ, etc. are also displayed on the display unit 10.

The operator confirms the position of the target T by looking at the display unit 10 (refer to FIG. 41) and determines whether or not the target T overlaps with the center point C of the endoscopic image. In FIG. 41, the target T is shifted from the center point C of the endoscopic image. Therefore, the operator adjusts the position and orientation of the endoscope 30 in such a manner that the target T overlaps with the center point C of the endoscopic image.

Figure 44:
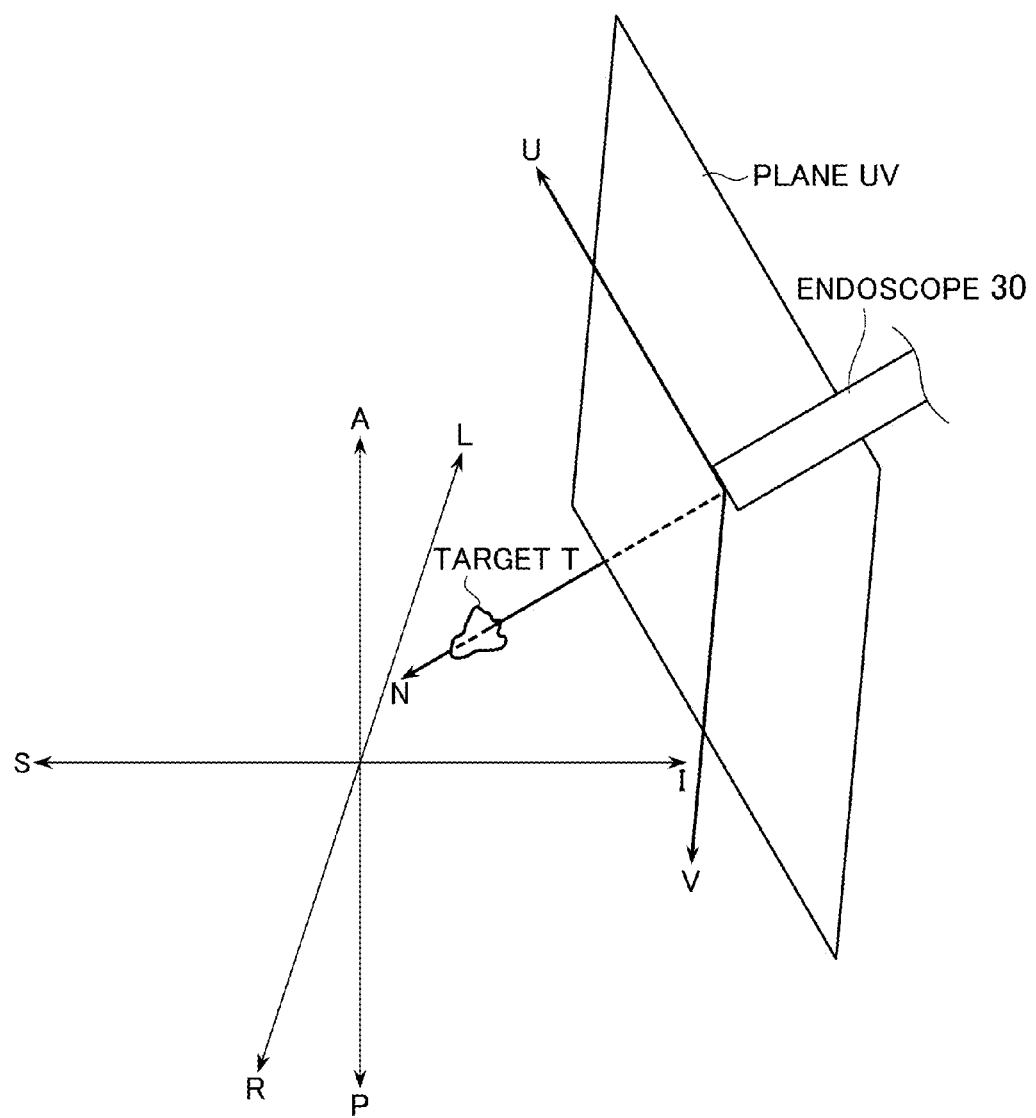
FIG. 44 is a diagram schematically showing the manner after the position and orientation of the endoscope are adjusted.
Figure 45A:
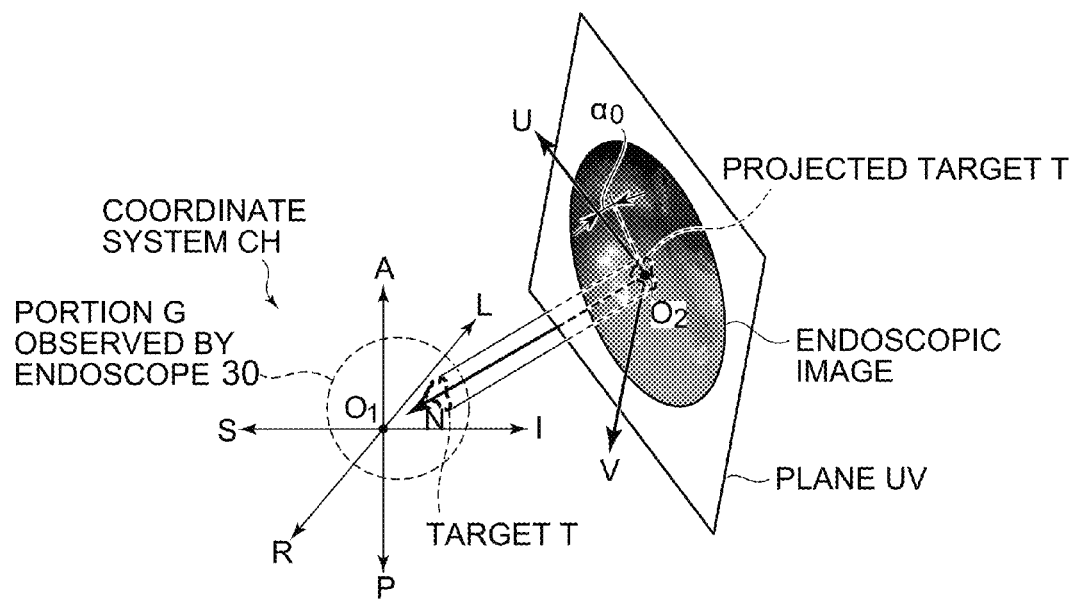
FIGS. 45A and 45B are a diagram for explaining a way of projecting the target T onto the endoscopic image.
Figure 45B:
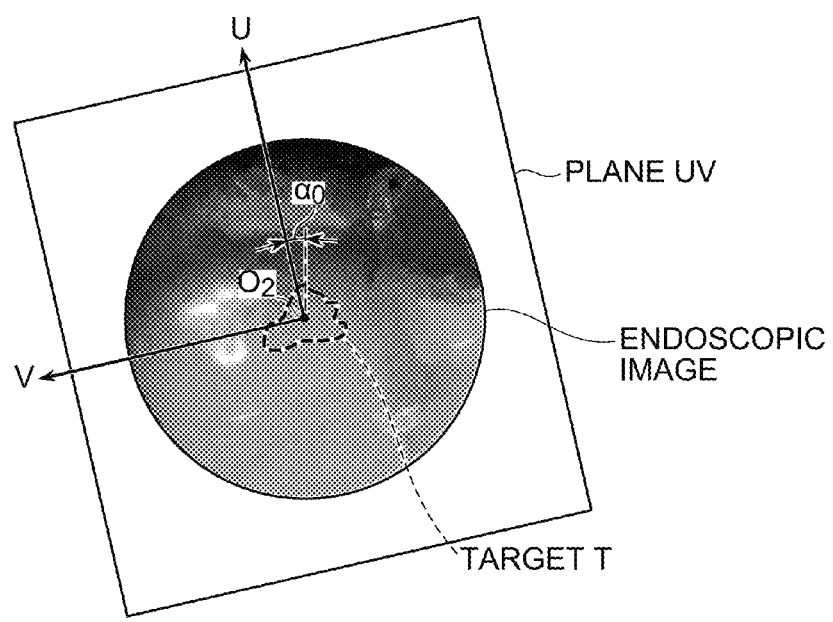

FIG. 44 is a diagram schematically showing the manner after the position and orientation of the endoscope 30 are adjusted. In FIG. 44, the vector N runs across the target T. In this case, the target T is projected onto the endoscopic image as follows:

FIGS. 45A and 45B are a diagram for explaining a way of projecting the target T onto the endoscopic image.

FIG. 45A is a diagram for explaining a way of projecting the target T onto the endoscopic image, and FIG. 45B is a diagram in the case where FIG. 45A is viewed from the direction of the vector N.

Figure 46:
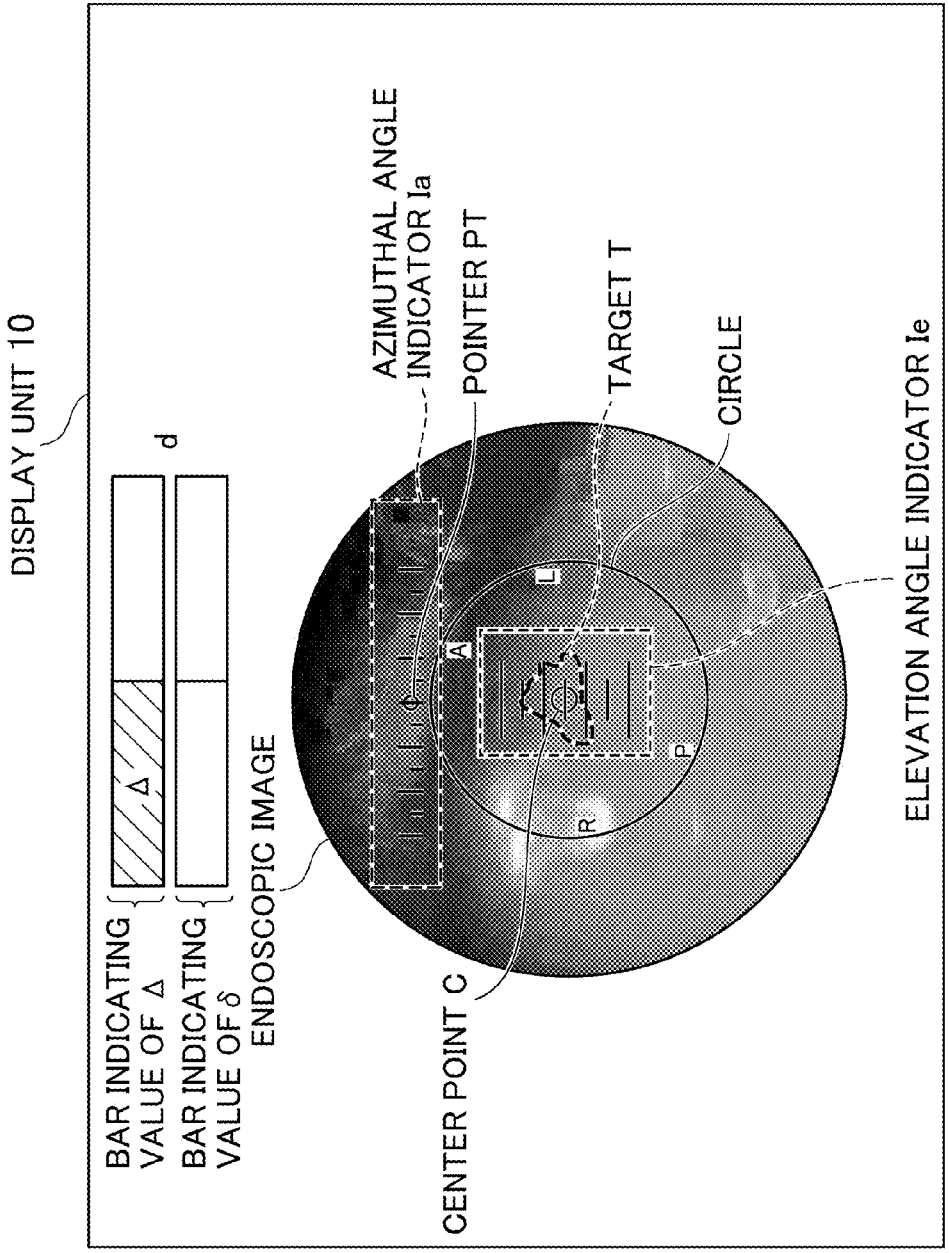
FIG. 46 is a diagram showing one example of the endoscopic image displayed on the display unit.

When the vector N crosses the target T, the target N is projected onto the center of the endoscopic image. Thus, looking at the endoscopic image displayed on the display unit 10, the target T has been displayed at the center point C of the endoscopic image as shown in FIG. 46. The operator sets the virtual protrusion distance δ of the surgical instrument 34 after having confirmed that the target T overlaps with the center point C of the endoscopic image (refer to FIG. 47).

Figure 47:
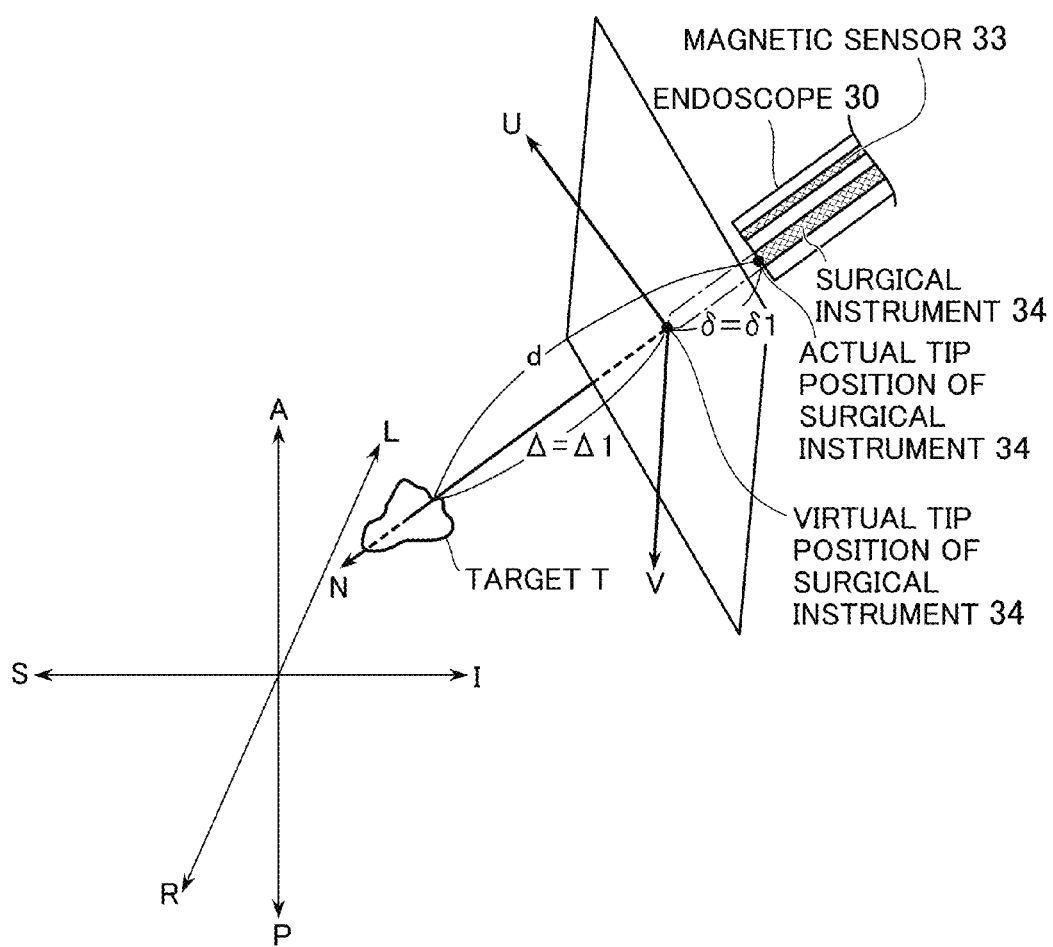
FIG. 47 is a diagram showing a situation in which the virtual protrusion distance δ of the surgical instrument is set to δ=δ1.

FIG. 47 is a diagram showing a situation in which the virtual protrusion distance δ of the surgical instrument 34 is set to δ=δ1.

Figure 48:
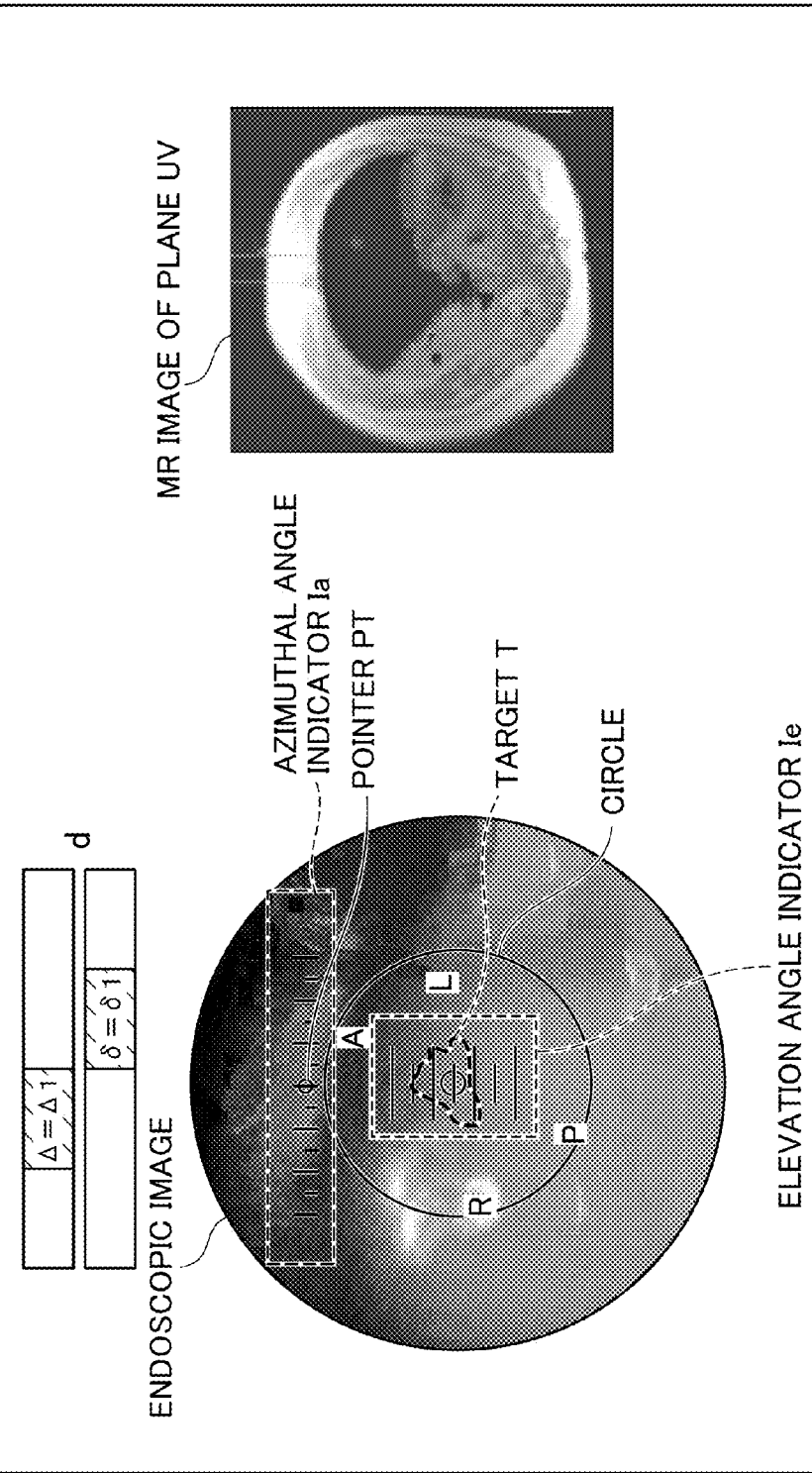
FIG. 48 is a diagram showing one example of an image displayed on the display unit.

When the protrusion distance δ=δ1 is set, the calculating unit 84 calculates the distance Δ and the like. Further, the MR apparatus performs a scan for acquiring an MR image of the plane UV. The MR image of the plane UV acquired by the scan is displayed on the display unit 10 together with the endoscopic image. FIG. 48 shows one example of the image displayed on the display unit 10.

In the case of δ=δ1, the virtual tip position of the surgical instrument 34 does not reach the target T (refer to FIG. 47). In this case, since the plane UV does not run across the target T, the operator is not able to confirm the target T within the MR image of the plane UV even though the operator looks at the MR image of the plane UV. Thus, the operator finds that the position of δ=δ1 is deviated from the position of the target T. Therefore, the operator sets δ to another value (refer to FIG. 49).

Figure 49:
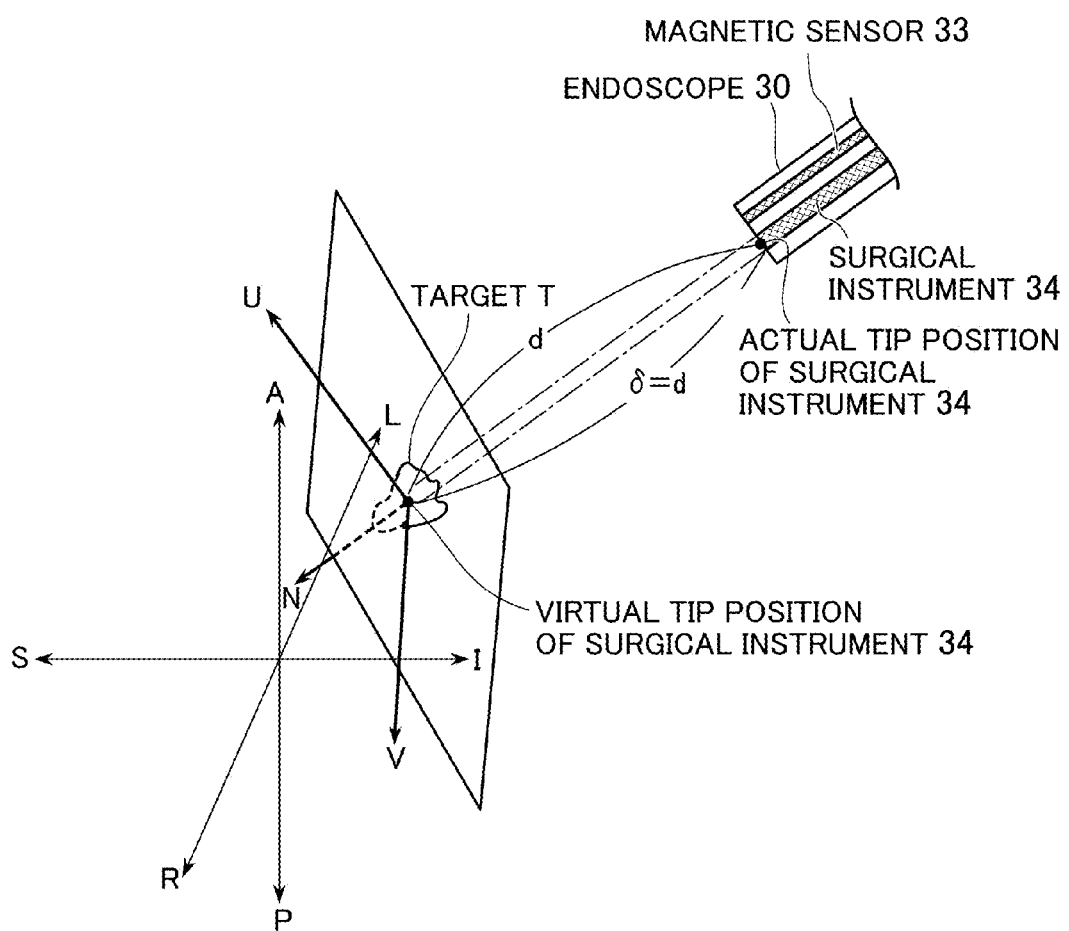
FIG. 49 is a diagram showing a situation in which the operator sets δ to another value.

FIG. 49 is a diagram showing a situation in which the operator sets δ to another value.

Figure 50:
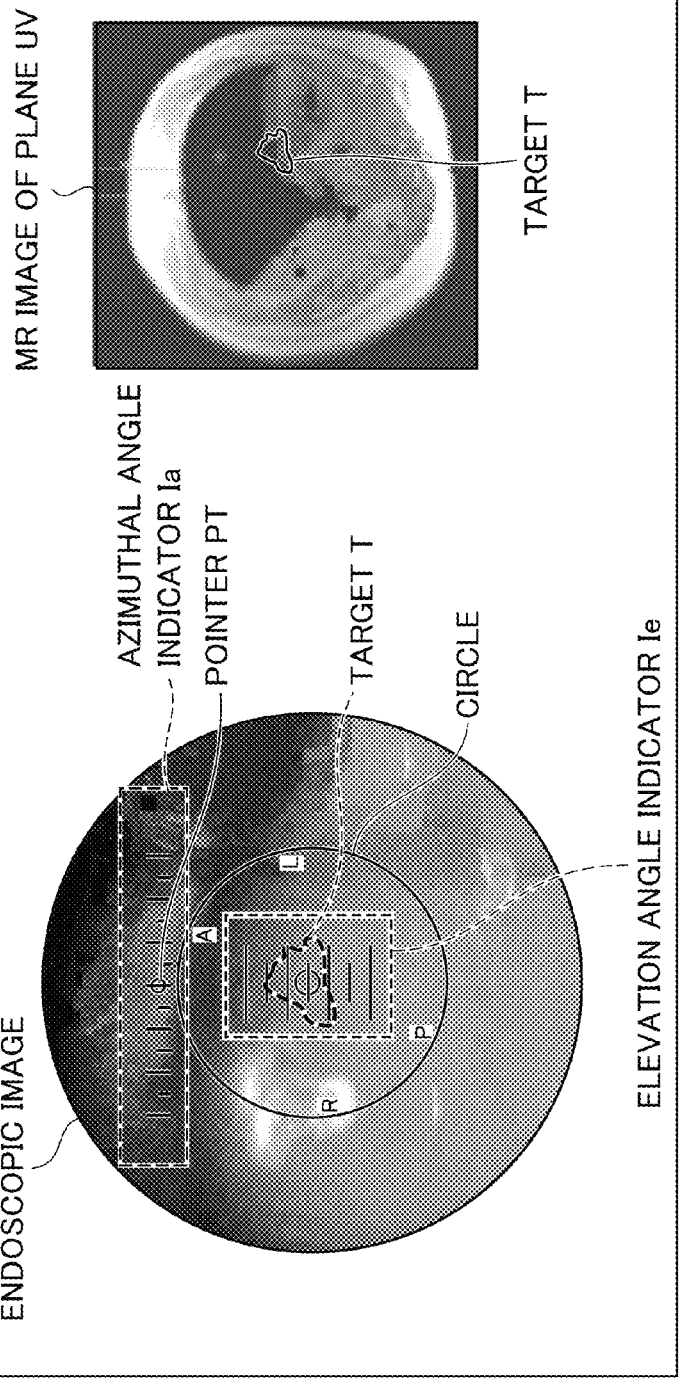
FIG. 50 is a diagram showing one example of an image displayed on the display unit.

There is shown in FIG. 49, an example in which δ is set to δ=d. In this case, the virtual tip position of the surgical instrument 34 has reached the target T. The MR apparatus performs a scan for acquiring an MR image of the plane UV. In this case, such an image as illustrated in FIG. 50 is displayed on the display unit 10.

Since the virtual tip position of the surgical instrument 34 reaches the target T where δ=d (refer to FIG. 49), the operator is able to confirm the target T within the MR image of the plane UV.

Subsequently, in the same manner as above, the operator changes the value of δ and confirms MR images of the plane UV obtained for each value of δ. Thus, by confirming the MR images of the plane UV obtained for each value of δ, the operator is able to confirm information such as the position, size and form of the target T. After the operator has confirmed the position, size, form, etc. of the target T, the operator actually protrudes the surgical instrument 34 from the distal end of the endoscope 30 and provides a surgical procedure to the target T to perform treatment.

In the fourth embodiment, the operator is able to confirm a positional relationship between the endoscopic image and the target T by looking at the display unit 10. Further, since the distance from the virtual tip position of the surgical instrument 34 to the target T can also be recognized by calculating the distance Δ, the operator can use the distance Δ as reference when the operator sets the value of δ.

Incidentally, in the fourth embodiment, although the MR image of the plane UV is displayed, the MR images of the planes NU and NV (refer to FIG. 4) may further be displayed. FIG. 51 is a diagram showing one example in which the MR image of the plane UV, the MR image of the plane NU and the MR image of the plane NV are displayed. Since the operator is able to confirm the MR images of the three planes orthogonal to each other by displaying these MR images, it is possible for the operator to smoothly adjust the position or orientation of the distal end of the endoscope 30.

Further, the first to fourth embodiments respectively have described the magnetic resonance apparatus. However, the systems and methods described herein can be applied to a medical apparatus which is different from the magnetic resonance apparatus (e.g., CT apparatus), when the medical apparatus has a display device displaying an endoscopic image.

Furthermore, the first to fourth embodiments respectively have described the example in which the endoscopic image of the animal 11 is acquired. In the disclosure, however, the object to be observed by the endoscope is not limited to the animal, but a human body and an object (e.g., the inside of piping or the interior of a building) other than an organism can be assumed to be an object to be observed by the endoscope.

What is claimed is:

1. A display device configured to display an endoscopic image obtained by an endoscope for observing an object, the display device comprising:
    a projecting unit configured to project a plurality of coordinate axes set to the object onto the endoscopic image such that an origin of the plurality of coordinate axes is aligned with a protruding direction of the endoscope;
    a display unit configured to display thereon the endoscopic image and the plurality of coordinate axes projected onto the endoscopic image; and
    a selecting unit configured to select a coordinate axis to be displayed on the display unit from among the plurality of coordinate axes, wherein the display unit is configured to display the coordinate axis selected by the selecting unit.

2. The display device according to claim 1, wherein the selecting unit is configured to select the coordinate axis on the basis of an angle formed between each of the plurality of coordinate axes and a view direction of the endoscope.

3. The display device according to claim 1, further comprising a first calculating unit configured to calculate an angle of a distal end of the endoscope.

4. The display device according to claim 3, wherein the first calculating unit is configured to calculate an elevation angle of the distal end of the endoscope.

5. The display device according to claim 3, wherein the first calculating unit is configured to calculate an azimuthal angle of the distal end of the endoscope.

6. The display device according to claim 1, further comprising a surgical instrument for performing a surgical procedure on a target for the object, which is provided at the distal end of the endoscope, wherein the surgical instrument is capable of protruding in the view direction of the endoscope.

7. The display device according to claim 6, wherein the display unit is configured to display the target for the object.

8. The display device according to claim 6, further comprising a second calculating unit configured to calculate a distance from the position of the distal end of the endoscope to the target for the object.

9. The display device according to claim 8, wherein the display unit is configured to display a distance from the position of the distal end of the endoscope to the target for the object.

10. The display device according to claim 6, wherein the endoscope is configured to be capable of setting a virtual protrusion distance of the surgical instrument when the surgical instrument is assumed to be protruded from the distal end of the endoscope.

11. The display device according to claim 10, wherein the display unit is configured to display the protrusion distance.

12. A medical apparatus comprising a display device configured to display an endoscopic image obtained by an endoscope for observing an object, the display device comprising:
- a projecting unit configured to project a plurality of coordinate axes set to the object onto the endoscopic image such that an origin of the plurality of coordinate axes is aligned with a protruding direction of the endoscope;
- a display unit configured to display thereon the endoscopic image and the plurality of coordinate axes projected onto the endoscopic image; and
- a selecting unit configured to select a coordinate axis to be displayed on the display unit from among the plurality of coordinate axes, wherein the display unit is configured to display the coordinate axis selected by the selecting unit.

13. The medical apparatus according to claim 12, wherein the selecting unit is configured to select the coordinate axis on the basis of an angle formed between each of the plurality of coordinate axes and a view direction of the endoscope.

14. The medical apparatus according to claim 12, further comprising a first calculating unit configured to calculate an angle of a distal end of the endoscope.

* * * * *